United States Patent

Yamada et al.

(10) Patent No.: US 12,054,588 B2
(45) Date of Patent: Aug. 6, 2024

(54) ORGANOPOLYSILOXANE COMPOUND, METHOD FOR PRODUCING SAME, AND ANTISTATIC AGENT AND CURABLE COMPOSITION, EACH OF WHICH CONTAINS SAME

(71) Applicant: SHIN-ETSU CHEMICAL CO., LTD., Tokyo (JP)

(72) Inventors: Tetsuro Yamada, Annaka (JP); Masahiko Minemura, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 742 days.

(21) Appl. No.: 17/268,810

(22) PCT Filed: Jul. 11, 2019

(86) PCT No.: PCT/JP2019/027497
§ 371 (c)(1),
(2) Date: Feb. 16, 2021

(87) PCT Pub. No.: WO2020/036022
PCT Pub. Date: Feb. 20, 2020

(65) Prior Publication Data
US 2021/0355284 A1    Nov. 18, 2021

(30) Foreign Application Priority Data

Aug. 17, 2018    (JP) .................................. 2018-153577

(51) Int. Cl.
*C08G 77/26* (2006.01)
*C08F 290/06* (2006.01)
(Continued)

(52) U.S. Cl.
CPC .......... *C08G 77/26* (2013.01); *C08F 290/068* (2013.01); *C08G 77/16* (2013.01);
(Continued)

(58) Field of Classification Search
CPC ...... C08G 77/26; C08G 77/30; C08G 77/388; C08G 77/395; C08F 230/08; G02B 1/04; G02B 1/043

See application file for complete search history.

(56) References Cited

U.S. PATENT DOCUMENTS

| | | | | |
|---|---|---|---|---|
| 5,358,688 A | * | 10/1994 | Robertson | ............. C08F 230/08 424/78.22 |
| 2007/0161768 A1 | * | 7/2007 | Odaka | .................. C08G 65/336 528/25 |

(Continued)

FOREIGN PATENT DOCUMENTS

| | | |
|---|---|---|
| JP | 6-128379 A | 5/1994 |
| JP | 6-256421 A | 9/1994 |

(Continued)

OTHER PUBLICATIONS

Extended European Search Report issued Apr. 12, 2022, in European Patent Application No. 19849244.9.
(Continued)

*Primary Examiner* — Marc S Zimmer
(74) *Attorney, Agent, or Firm* — Birch, Stewart, Kolasch & Birch, LLP

(57) ABSTRACT

An organopolysiloxane compound represented by average structural formula (1) is capable of imparting an electron beam curable resin with high antistatic properties, while having excellent antistatic performance durability.

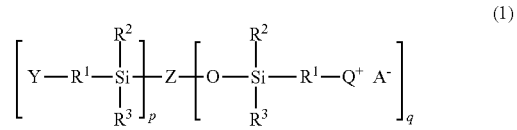

(1)

(In the formula, Z represents a single bond or a group having a functionality of 2-20 and containing an organopolysiloxane structure; $R^1$ represents a single bond, or an unsubstituted or substituted alkylene group having 1-20 carbon atoms; each of $R^2$ and $R^3$ represents an unsubstituted or substituted alkyl group having 1-10 carbon atoms, or the like; Y represents a monovalent hydrocarbon group having a polymerizable reactive group; each of p and q represents a number of 1-10, with (p+q) being 2-20 in accordance with the valence of Z; and in cases where Z represents a single bond, p and q represent 1, $A^-$ represents an anion and $Q^+$ represents a cationic group that is represented by one of formulae (2)-(4)

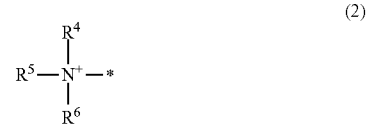

(2)

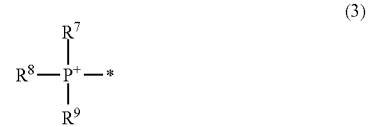

(3)

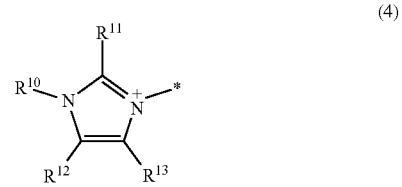

(4)

(Continued)

(wherein each one of $R^4$-$R^{10}$ represents an alkyl group having 1-20 carbon atoms, or the like; each one of $R^{11}$-$R^{13}$ represents a hydrogen atom or the like; and * represents a bonding hand).)

12 Claims, No Drawings

(51) Int. Cl.
*C08G 77/16* (2006.01)
*C08G 77/20* (2006.01)
*C08G 77/30* (2006.01)
*C08G 77/388* (2006.01)
*C08G 77/395* (2006.01)
*C09D 4/00* (2006.01)
*C09D 183/08* (2006.01)
*C09K 3/16* (2006.01)

(52) U.S. Cl.
CPC .............. *C08G 77/20* (2013.01); *C08G 77/30* (2013.01); *C08G 77/388* (2013.01); *C08G 77/395* (2013.01); *C09D 4/00* (2013.01); *C09D 183/08* (2013.01); *C09K 3/16* (2013.01)

(56) References Cited

U.S. PATENT DOCUMENTS

| | | | | |
|---|---|---|---|---|
| 2008/0182956 | A1* | 7/2008 | Stanbro | C08G 77/388 526/260 |
| 2012/0136087 | A1* | 5/2012 | Parakka | A61L 31/06 523/105 |
| 2016/0176902 | A1* | 6/2016 | Tay | C08F 230/085 526/279 |

FOREIGN PATENT DOCUMENTS

| | | | | |
|---|---|---|---|---|
| JP | 2000-282014 A | | 10/2000 | |
| JP | 2010-248165 A | | 11/2010 | |
| JP | 2014-227361 A | | 12/2014 | |
| JP | 2017-75237 A | | 4/2017 | |
| JP | 2019147771 A | * | 9/2019 | ......... F16H 25/2214 |
| JP | 2020094139 A | * | 6/2020 | |
| WO | WO 2015/163022 A1 | | 10/2015 | |

OTHER PUBLICATIONS

International Search Report for PCT/JP2019/027497 mailed on Oct. 8, 2019.
Written Opinion of the International Searching Authority for PCT/JP2019/027497 (PCT/ISA/237) mailed on Oct. 8, 2019.

* cited by examiner

ORGANOPOLYSILOXANE COMPOUND, METHOD FOR PRODUCING SAME, AND ANTISTATIC AGENT AND CURABLE COMPOSITION, EACH OF WHICH CONTAINS SAME

TECHNICAL FIELD

The present invention relates to an organopolysiloxane compound, to a method for preparing the same and to an antistatic agent and a curable composition which contain such a compound. The invention relates more specifically to an organopolysiloxane compound that has on the molecule an organopolysiloxane structure and contains polymerizable reactive groups and ionic groups, to a method for preparing the compound, and to an antistatic agent and a curable composition which include such an organopolysiloxane compound.

BACKGROUND ART

It has been reported that onium salts in which the cation is an ammonium or phosphonium ion having a trialkoxysilylalkyl group and the anion is a perfluoroalkylsulfonyl imide ion can be used as oligomeric antistatic agents for fluoroplastics (see Patent Document 1).

However, the inventors, on using one such onium salt, 1-(3-trimethoxysilylpropyl)-1,1,1-tributylphosphonium bis(trifluoromethanesulfonyl)imide, as an antistatic agent in an electron beam-curable acrylic resin, learned that it is unable to confer a practical antistatic performance.

Patent Document 2 discloses, as a compound capable of enhancing the antistatic performance, a siloxane copolymer obtained by copolymerizing an onium salt having an alkoxysilyl group with a dialkoxysilane.

However, when the inventors used this siloxane copolymer as an antistatic agent in an electron beam-curable acrylic resin, they learned that the initial antistatic performance is excellent, but because the molecule has no polymerizable reactive groups capable of reacting with the electron beam-curable acrylic resin, the durability, especially the water resistance, is inadequate and so the antistatic performance decreases over time due to contact with water.

PRIOR ART DOCUMENTS

Patent Documents

Patent Document 1: JP-A 2010-248165
Patent Document 2: WO 2015/163022

SUMMARY OF INVENTION

Technical Problem

In view of the above circumstances, the objects of the invention are to provide an organopolysiloxane compound that can confer an electron beam-curable resin with high antistatic properties and that moreover has an excellent antistatic performance durability, a method for preparing such a compound, and also an antistatic agent and a curable composition containing such an organopolysiloxane compound.

Solution to Problem

The inventors have conducted extensive investigations aimed at achieving these objects. As a result, they have discovered a specific organopolysiloxane compound that has on the molecule an organopolysiloxane structure and contains a polymerizable reactive group and an ionic group, and a method for preparing such a compound. They have also discovered that not only does this organopolysiloxane compound confer electron beam-curable resins with high antistatic properties, the durability of the antistatic performance is also excellent. These discoveries ultimately led to the present invention.

Accordingly, the present invention provides:
1. An organopolysiloxane compound represented by average structural formula (1)

[Chem. 1]

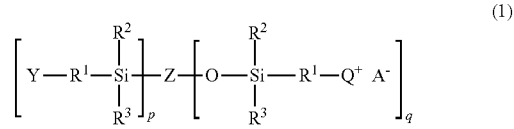

[wherein Z is a single bond or a 2 to 20-valent group which includes an organopolysiloxane structure; each $R^1$ is independently a single bond or a substituted or unsubstituted alkylene group of 1 to 20 carbon atoms; $R^2$ and $R^3$ are each independently a substituted or unsubstituted alkyl group of 1 to 10 carbon atoms or aryl group of 6 to 10 carbon atoms; each Y is independently a polymerizable reactive group-containing monovalent hydrocarbon group; p is a number from 1 to 10, q is a number from 1 to 10, and p+q is a number from 2 to 20 corresponding to the valence of Z, with the proviso that when Z is a single bond, p and q are both 1; $A^-$ is a monovalent anion; and $Q^+$ is a monovalent cationic group represented by any one of formulas (2) to (4) below

[Chem. 2]

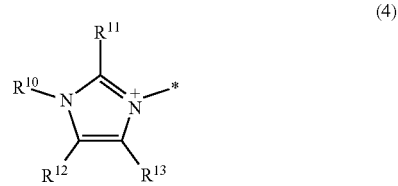

(wherein $R^4$ to $R^{10}$ are each independently an alkyl group of 1 to 20 carbon atoms, an aryl group of 6 to 20 carbon atoms or an aralkyl group of 7 to 20 carbon atoms; $R^{11}$ to $R^{13}$ are each independently a hydrogen atom, an alkyl group of 1 to 20 carbon atoms or an aryl group of 6 to 20 carbon atoms; $R^4$ and $R^5$ may mutually bond to form, together with the nitrogen atom, a pyrrolidine ring which may have a substituent, a piperidine ring which may have a substituent or a pyridine ring which may have a substituent; $R^7$ and $R^8$ may mutually bond to form, together with the phosphorus atom, a phosphorane ring which may have a substituent, a phosphorinane ring which may have a substituent or a phosphorine ring which may have a substituent; and * represents a site available for bonding; with the provisos that when $R^4$ and $R^5$ mutually bond to form a pyridine ring, $R^6$ does not exist, and when $R^7$ and $R^8$ mutually bond to form a phosphorine ring, $R^9$ does not exist)].

2. The organopolysiloxane compound of 1 above, wherein the polymerizable reactive group Y is of one type selected from (meth)acryloyloxy groups and (meth)acrylamide groups.

3. The organopolysiloxane compound of 1 or 2 above, wherein $A^-$ is a fluorine-containing anion or a halide ion.

4. The organopolysiloxane compound of any of 1 to 3 above, wherein $A^-$ is a trifluoromethanesulfonic acid anion, a nonafluorobutanesulfonic acid anion, a bis(fluorosulfonyl)imide anion, a bis(trifluoromethanesulfonyl)imide anion, a tetrafluoroborate anion, a hexafluorophosphate anion, a chloride ion, a bromide ion or an iodide ion.

5. The organopolysiloxane compound of any of 1 to 4 above which is represented by average structural formula (5)

[Chem. 3]

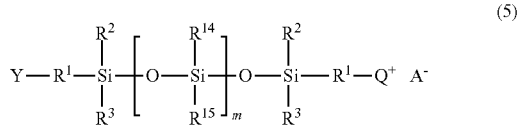

(5)

(wherein $R^1$, $R^2$, $R^3$, Y, $A^-$ and $Q^+$ are as defined above, $R^{14}$ and $R^{15}$ are each independently a substituted or unsubstituted alkyl group of 1 to 20 carbon atoms or aryl group of 6 to 10 carbon atoms, and m is a number of 0 or more).

6. A method of preparing the organopolysiloxane compound of any of 1 to 5 above which includes the step of reacting a polymerizable reactive group and silanolic hydroxyl group-containing organopolysiloxane compound of average structural formula (6)

[Chem. 4]

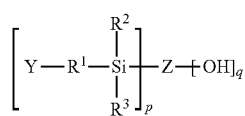

(6)

(wherein $R^1$, $R^2$, $R^3$, Y, p, q and Z are as defined above, and OH is a silanolic hydroxyl group) with a compound of formula (7)

[Chem. 5]

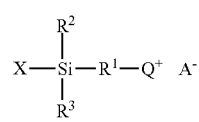

(7)

(wherein $R^1$, $R^2$, $R^3$, $A^-$ and $Q^+$ are as defined above, and X is a leaving group selected from alkoxy groups of 1 to 10 carbon atoms, halogen atoms and a hydroxyl group) having a functional group capable of reacting with the silanolic hydroxyl group and having an ionic group.

7. A method of preparing the organopolysiloxane compound of 5 above which includes the step of reacting a polymerizable reactive group and silanolic hydroxyl group-containing organopolysiloxane compound of average structural formula (8)

[Chem. 6]

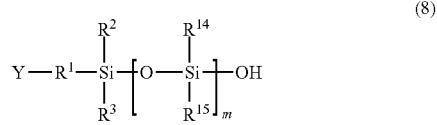

(8)

(wherein $R^1$, $R^2$, $R^3$, $R^{14}$, $R^{15}$, Y and m are as defined above) with a compound of formula (7)

[Chem. 7]

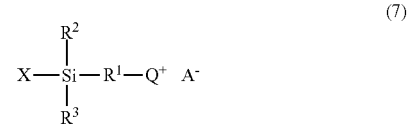

(7)

(wherein $R^1$, $R^2$, $R^3$, $A^-$, $Q^+$ and X are as defined above) having a functional group capable of reacting with the silanolic hydroxyl group and having an ionic group.

8. An antistatic agent which includes the organopolysiloxane compound of any of 1 to 5 above.

9. A curable composition which includes the organopolysiloxane compound of any of 1 to 5 above.

10. A coating material which includes the curable composition of 9 above.

11. A cured article obtained by curing the curable composition of 9 above.

12. A cured article having a coat obtained using the coating material of 10 above.

Advantageous Effects of Invention

Because the organopolysiloxane compound of the invention has on the molecule an organopolysiloxane structure, a polymerizable reactive group and an ionic group, compared with conventional antistatic agents, it can impart high antistatic properties and the resulting antistatic performance has an excellent durability.

Compositions which contain the organopolysiloxane compound of the invention having such properties can be suitably used as antistatic agents, curable compositions and coating materials.

DESCRIPTION OF EMBODIMENTS

The invention is described in detail below. The organopolysiloxane compound according to the invention is represented by average structural formula (1) (this compound is referred to below as Organopolysiloxane Compound (1)).

[Chem. 8]

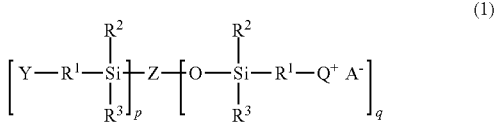

(1)

In formula (1), each $R^1$ is independently a single bond or a substituted or unsubstituted alkylene group of 1 to 20 carbon atoms, preferably 1 to 10 carbon atoms, and more preferably 1 to 3 carbon atoms.

The alkylene group of 1 to 20 carbon atoms may be linear, cyclic or branched. Specific examples include methylene, ethylene, trimethylene, propylene, n-butylene, isobutylene, n-pentylene, n-hexylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene and eicosadecylene groups.

Of these, linear alkylene groups are preferred; methylene, ethylene, trimethylene and octamethylene groups are more preferred; and methylene and trimethylene groups are even more preferred.

Some or all of the hydrogen atoms on these alkylene groups may be substituted with alkylene groups of 1 to 10 carbon atoms, halogen atoms such as fluorine, chlorine or bromine, cyano groups and the like.

$R^2$ and $R^3$ are each independently a substituted or unsubstituted alkyl group of 1 to 10 carbon atoms or aryl group of 6 to 10 carbon atoms. From the standpoint of the antistatic properties and the durability thereof, alkyl groups of 1 to 8 carbon atoms are preferred, and alkyl groups of 1 to 3 carbon atoms are more preferred.

The alkyl groups of 1 to 10 carbon atoms may be linear, cyclic or branched. Specific examples include methyl, ethyl, n-propyl, isopropyl, n-butyl, n-pentyl, n-hexyl, n-heptyl, n-octyl, n-nonyl and n-decyl groups. Linear alkyl groups are desirable, with methyl, n-propyl, n-hexyl and n-octyl groups being preferred, and methyl groups being more preferred.

Examples of aryl groups of 6 to 10 carbon atoms include phenyl and naphthyl groups. A phenyl group is preferred.

Some or all of the hydrogen atoms on the above alkyl groups and aryl groups may be substituted with alkyl groups of 1 to 10 carbon atoms, halogen atoms such as fluorine, chlorine and bromine, cyano groups and the like. Specific examples of such groups include 3-chloropropyl, 3,3,3-trifluoropropyl, 2-cyanoethyl, tolyl and xylyl groups. From the standpoint of the antistatic properties and the durability thereof, a 3,3,3-trifluoropropyl group is preferred.

Each Y independently represents a polymerizable reaction group-containing monovalent hydrocarbon group.

Specific examples of polymerizable reactive groups include (meth)acryloyloxy groups, (meth)acrylamide groups, styryl groups, vinyl groups, alkenyl groups, epoxy groups and maleimide groups. Of these, from the standpoint of the antistatic properties and the durability thereof, (meth)acryloyloxy groups, (meth)acrylamide groups, styryl groups and vinyl groups are preferred; (meth)acryloyloxy groups and (meth)acrylamide groups are more preferred.

$A^-$ represents a monovalent anion. Halide ions and fluorine-containing anions are preferred.

Specific examples of halide ions include chloride, bromide and iodide ions. From the standpoint of the antistatic properties and the durability thereof, a chloride ion is preferred.

Specific examples of fluorine-containing anions include the trifluoromethanesulfonate anion, nonafluorobutanesulfonate anion, bis(fluorosulfonyl)imide anion, bis(trifluoromethanesulfonyl)imide anion, tetrafluoroborate anion and hexafluorophosphate anion. From the standpoint of the antistatic properties and the durability thereof, the bis(fluorosulfonyl)imide anion and the bis(trifluoromethanesulfonyl)imide anion are preferred;

the bis(trifluoromethanesulfonyl)imide anion is more preferred.

$Q^+$ is a monovalent cationic group represented by any one of formulas (2) to (4) below

[Chem. 9]

(2)

(3)

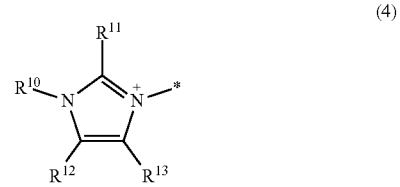

(4)

(wherein * represents a site available for bonding).

In the ammonium group represented by formula (2) (referred to below as "ammonium group (2)"), $R^4$ to $R^6$ are each independently an alkyl group of 1 to 20 carbon atoms, preferably 1 to 12 carbon atoms, an aryl group of 6 to 20 carbon atoms or an aralkyl group of 7 to 20 carbon atoms.

The alkyl groups of 1 to 20 carbon atoms may be linear, cyclic or branched. Specific examples include methyl, ethyl, n-propyl, isopropyl, n-butyl, n-pentyl, n-hexyl, n-heptyl, n-octyl, n-nonyl, n-decyl, undecyl, dodecyl and icosyl groups. From the standpoint of the antistatic properties and the durability thereof, linear alkyl groups are preferred; n-butyl, n-hexyl, n-octyl, n-nonyl, n-decyl, undecyl, dodecyl and icosyl groups are more preferred; n-butyl, and n-octyl groups are even more preferred, and the n-octyl group is still more preferred.

Specific examples of aryl groups of 6 to 20 carbon atoms include phenyl and naphthyl groups.

Specific examples of aralkyl groups of 7 to 20 carbon atoms include the benzyl group.

In the ammonium group (2), $R^4$ and $R^5$ may mutually bond to form a pyrrolidine ring of formula (2a) below which may have a substituent, a piperidine ring of formula (2b) below which may have a substituent or a pyridine ring of formula (2c) below which may have a substituent. However, in cases where $R^4$ and $R^5$ mutually bond at the ends to form a pyridine ring, as shown in formula (2c) below, $R^6$ does not exist.

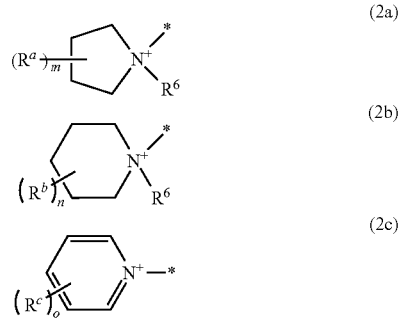

(wherein * represents a site available for bonding)

In formulas (2a), (2b) and (2c), Ra, $R^b$ and RC each represent an alkyl group of 1 to 20 carbon atoms, preferably 1 to 6 carbon atoms. These are exemplified by the same groups as those mentioned above as examples of $R^4$ to $R^6$.

Also, m is an integer from 0 to 8, preferably from 0 to 4, n is an integer from 0 to 10, preferably from 0 to 5, and o is an integer from 0 to 5.

In the phosphonium group of formula (3) (referred to below as "phosphonium group (3)"), $R^7$ to $R^9$ are each independently an alkyl group of 1 to 20 carbon atoms, an aryl group of 6 to 20 carbon atoms or an aralkyl group of 7 to 20 carbon atoms. Specific examples and preferred examples of these alkyl groups, aryl groups and aralkyl groups include the same groups as those mentioned above as examples of $R^4$ to $R^6$.

Also, in the phosphonium group (3), $R^7$ and $R^8$ may mutually bond to form a phosphorane ring of formula (3a) below which may have a substituent, a phosphorinane ring to of formula (3b) below which may have a substituent or a phosphorine ring of formula (3c) below which may have a substituent. However, in cases where $R^7$ and $R^8$ mutually bond to form a phosphorine ring, as shown in formula (3c) below, $R^9$ does not exist.

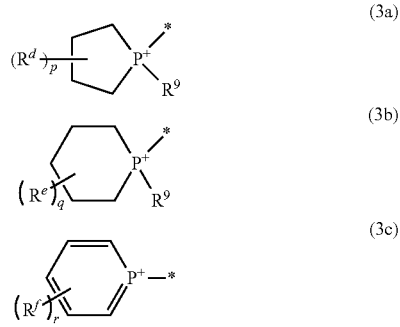

(wherein * represents a site available for bonding)

In formulas (3a), (3b) and (3c), $R^d$, $R^e$ and $R^f$ each represent an alkyl group of 1 to 20 carbon atoms, preferably 1 to 6 carbon atoms. These are exemplified by the same groups as those listed above as examples of $R^4$ to $R^6$.

Also, p is an integer from 0 to 8, preferably from 0 to 4, q is an integer from 0 to 10, preferably from 0 to 5, and r is an integer from 0 to 5.

In the imidazonium group of formula (4) (referred to below as "imidazonium group (4)"), $R^1$ represents an alkyl group of 1 to 20 carbon atoms, an aryl group of 6 to 20 carbon atoms or an aralkyl group of 7 to 20 carbon atoms; and $R^{11}$ to $R^{13}$ each independently represent a hydrogen atom, an alkyl group of 1 to 20 carbon atoms, an aryl group of 6 to 20 carbon atoms or an aralkyl group of 7 to 20 carbon atoms. Specific examples and preferred examples of these alkyl groups, aryl groups and aralkyl groups include the same groups as those mentioned above as examples of $R^4$ to $R^6$.

Also, in formula (1), Z represents a single bond or a 2 to 20-valent group that includes an organopolysiloxane structure.

The organopolysiloxane structure-containing group represented by Z is not particularly limited, and may have therein a linear structure, a branched structure or a cross-linked structure.

More specific examples include organopolysiloxane structures consisting of D units ($R^2{}_2SiO_{2/2}$ units), T units ($R^2SiO_{3/2}$ units) and Q units ($SiO_{4/2}$ units) (in these formulas, $R^2$ is as defined above).

These units may be of one type used alone (D units only, T units only, or Q units only), or a plurality of different units may be used in combination. From the standpoint of the antistatic properties and the durability thereof, an organopolysiloxane structure containing D units is preferred, and an organopolysiloxane structure of D units alone is more preferred.

The subscript "p" in formula (1) represents the number of monovalent hydrocarbon groups having a polymerizable reactive group, and q represents the number of ionic groups.

The average of p per molecule is from 1 to 10, preferably from 1 to 5, more preferably from 1 to 2, and even more preferably 1. When p is less than 1, there are too few polymerizable reactive groups and so the durability is inferior. On the other hand, when p exceeds 10, there are too many reactive sites, as a result of which the storage stability of the compound worsens or the antistatic properties worsen.

The average of q per molecule is from 1 to 10, preferably from 1 to 5, more preferably from 1 to 2, and even more preferably 1. When q is less than 1, there are too few ionic groups, and so the antistatic properties are inferior. On the other hand, when q exceeds 10, there are too many ionic groups, as a result of which the storage stability of the compound may worsen or the physical properties of cured products containing the organopolysiloxane compound of the invention may worsen.

In this invention, the sum of p and q corresponds to the valence of the organopolysiloxane structure-containing group represented by Z. The average valence of Z per molecule is, as mentioned above, from 2 to 20, and is preferably from 2 to 10, more preferably from 2 to 4, and even more preferably 2. When the valence of Z is less than 2, there are too few polymerizable reactive groups and ionic groups, resulting in poor antistatic properties and a poor durability thereof. On the other hand, when the valence of Z is greater than 20, there are too many polymerizable reactive groups and ionic groups, as a result of which the storage stability of the compound may worsen or the antistatic properties may worsen.

When Z is a single bond, the molecule has a form in which the silicon and oxygen on either side of Z bond directly to each other, and so p and q are both 1.

The organopolysiloxane compound of the invention is preferably one represented by average structural formula (5) below, wherein Z is a single bond or an organopolysiloxane structure of D units only. When such a compound is used, even better antistatic properties and an even better durability thereof are exhibited.

[Chem. 12]

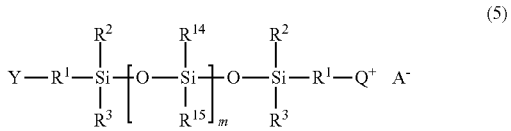

(5)

(wherein $R^1$, $R^2$, $R^3$, Y, $A^-$ and $Q^+$ are as defined above)

In formula (5), $R^{14}$ and $R^{15}$ are each independently a substituted or unsubstituted alkyl group of 1 to 20 carbon atoms or aryl group of 6 to 10 carbon atoms. Specific examples of these alkyl groups and aryl groups are the same as those mentioned above for $R^2$ to $R^6$.

Of these, from the standpoint of the antistatic properties and the durability thereof, the alkyl group is preferably a linear alkyl group, more preferably an alkyl group of 1 to 3 carbon atoms, and even more preferably a methyl group. The aryl group is preferably a phenyl group.

Also, m represents a number of 0 or more. However, from the standpoint of the antistatic properties and the durability thereof, m is preferably from 0 to 1,000, more preferably from 3 to 100, and even more preferably from 6 to 50.

The weight-average molecular weight of the organopolysiloxane compound of the invention is not particularly limited. However, in order to impart sufficient antistatic properties and a sufficient durability thereof to cured products obtained by curing a curable composition containing this compound, the weight-average molecular weight is preferably from 500 to 100,000, more preferably from 700 to 10,000, and even more preferably from 1,000 to 5,000. The weight-average molecular weight in this invention is a polystyrene-equivalent value obtained by gel permeation chromatography (GPC).

The organopolysiloxane compound of the invention may be used in a solvent-containing state.

The solvent is not particularly limited, so long as it has the ability to dissolve the organopolysiloxane compound (1). However, from the standpoint of the solvency, volatility and the like, aromatic solvents such as toluene and xylene, ketone solvents such as methyl ethyl ketone and methyl isobutyl ketone, ether solvents such as tetrahydrofuran, and nitrile solvents such as acetonitrile are preferred. Of these, methyl ethyl ketone, methyl isobutyl ketone and acetonitrile are more preferred.

The amount of solvent added per 100 parts by weight of the organopolysiloxane compound (1) is preferably from 100 to 20,000 parts by weight, and more preferably from 200 to 10,000 parts by weight.

The organopolysiloxane compound (1) can be obtained by reacting a polymerizable reactive group and silanolic hydroxyl group-containing organopolysiloxane compound of average structural formula (6) below (referred to below as "silanolic hydroxyl group-containing organopolysiloxane compound (6)") with a compound of formula (7) below having a functional group capable of reacting with the silanolic hydroxyl group and having an ionic group (referred to below as "ionic compound (7)").

More specifically, a reaction is carried out that forms a siloxane bond via the reaction mechanism of a dehydrohalogenation or dehydration reaction between the silanolic hydroxyl group on the silanolic hydroxyl group-containing organopolysiloxane compound (6) and the leaving group on the ionic compound (7).

[Chem. 13]

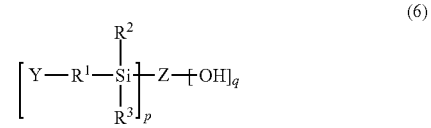

(6)

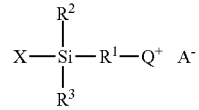

(7)

(wherein $R^1$, $R^2$, $R^3$, Y, p, q, Z, $A^-$ and $Q^+$ are as defined above, OH is a silanolic hydroxyl group, and X is a leaving group selected from alkoxy groups of 1 to 10 carbon atoms, halogen atoms and a hydroxyl group (—OH group))

In the alkoxy group of 1 to 10 carbon atoms represented by X, the alkyl group may be linear, cyclic or branched. Specific examples include methoxy, ethoxy, n-propoxy, isopropoxy, n-butoxy, t-butoxy, n-pentoxy, n-hexyloxy, n-heptyloxy, n-octyloxy, n-nonyloxy and n-decyloxy groups. From the standpoint of the reactivity, an alkoxy group of 1 to 3 carbon atoms is preferred, a methoxy or ethoxy group is more preferred, and a methoxy group is even more preferred.

Examples of the halogen atom include chlorine, bromine and iodine atoms. From the standpoint of the reactivity, a chlorine atom is preferred.

Specific examples of the silanolic hydroxyl group-containing organopolysiloxane compound (6) include, but are not limited to, those of the following structural formulas.

[Chem. 14]

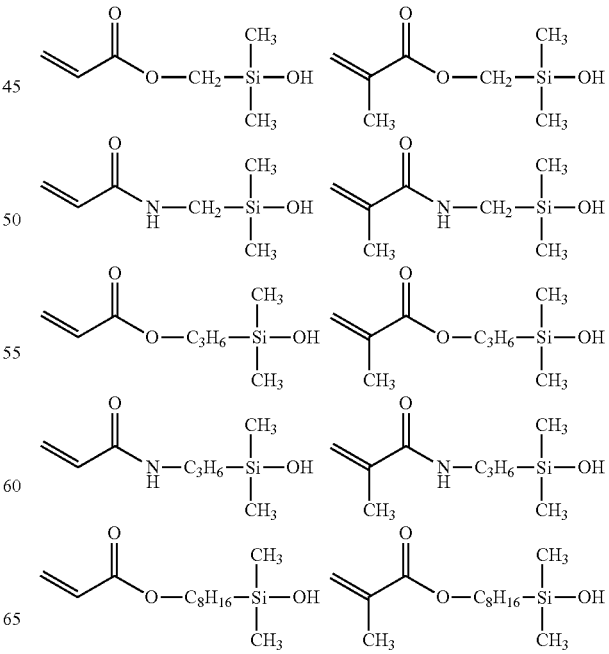

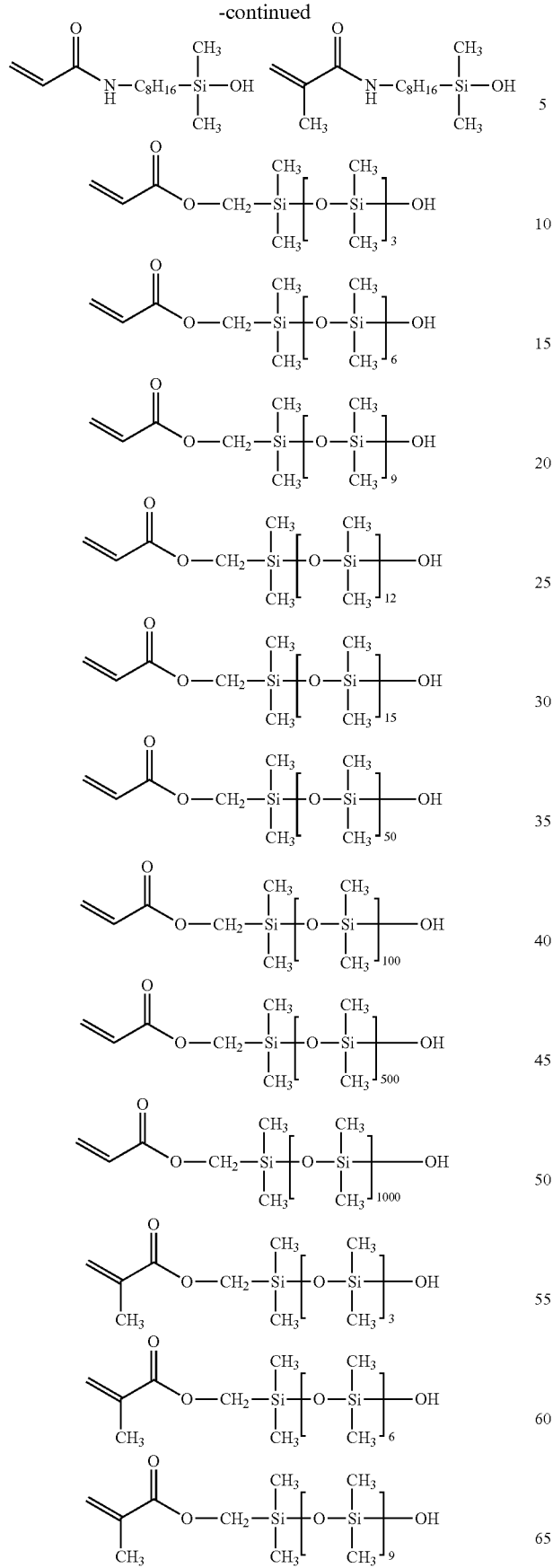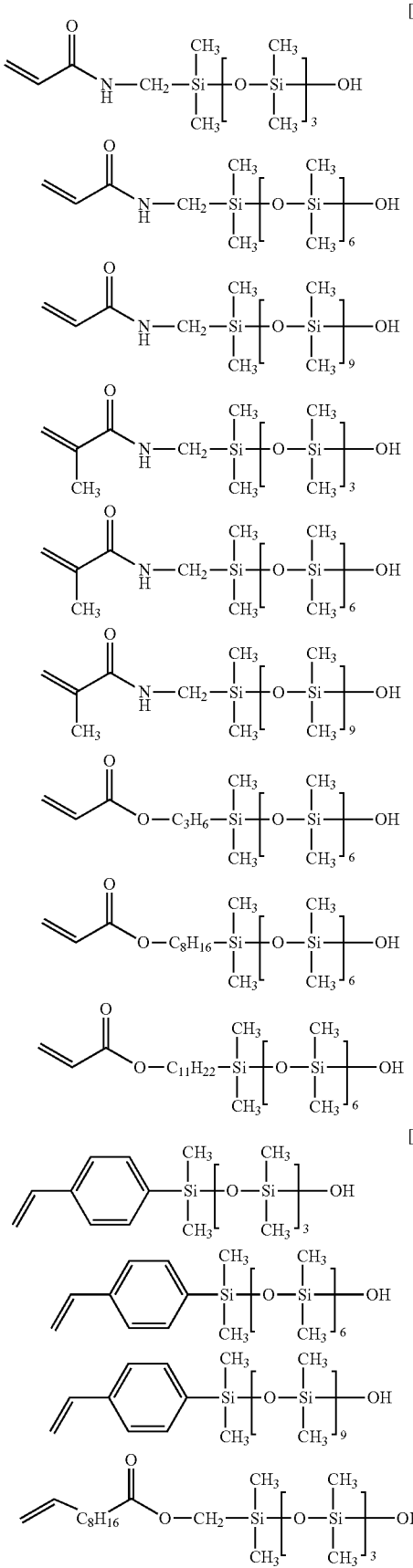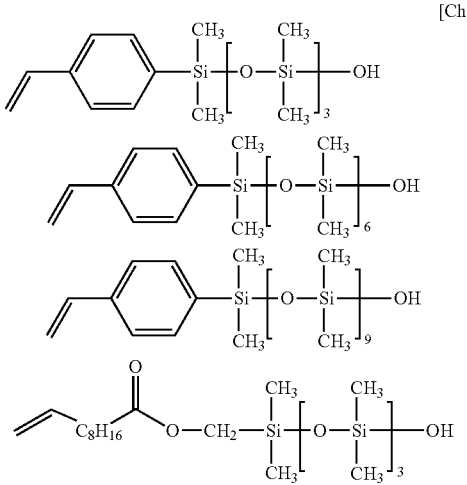

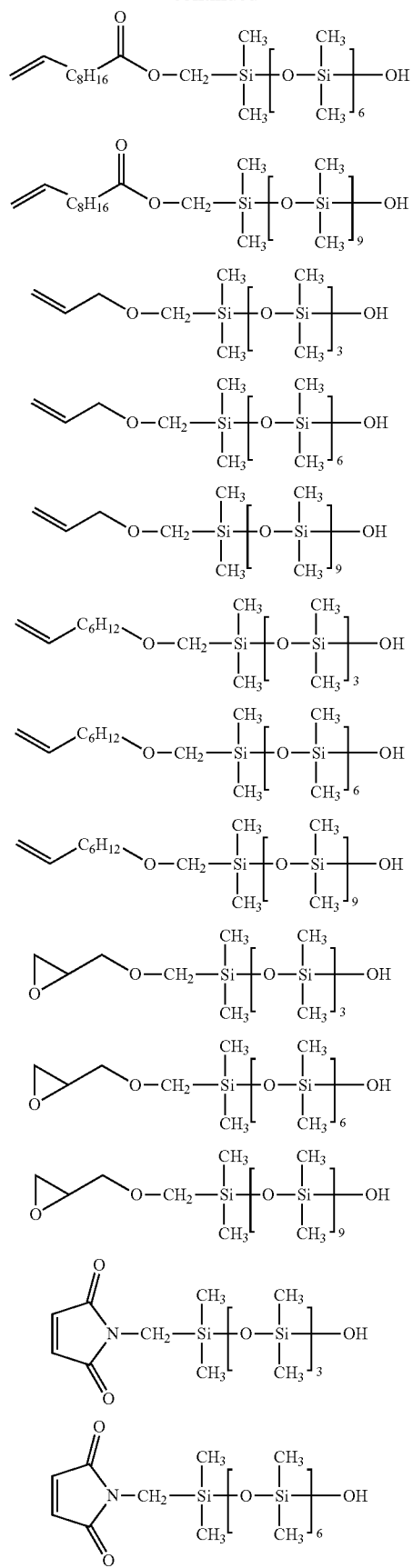
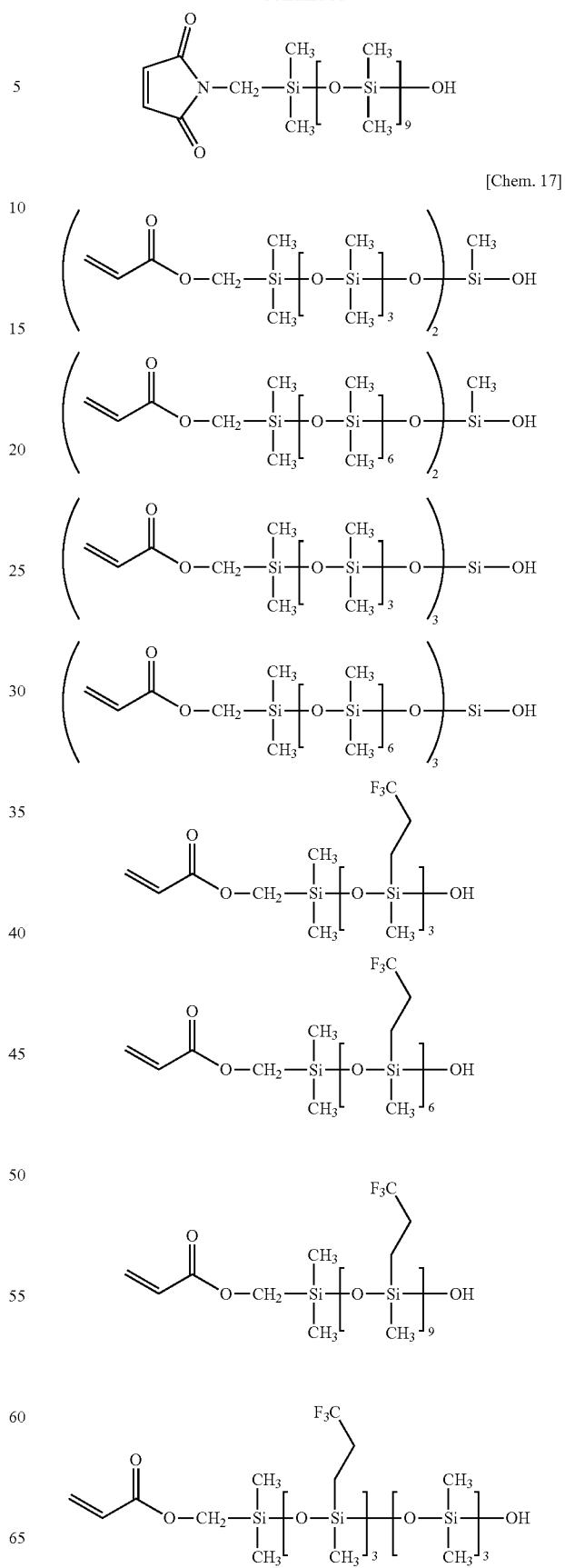

-continued

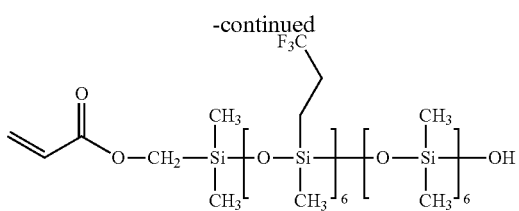

Specific examples of the ionic compound (7) include, but are not limited to, tributyl{(chlorodimethylsilyl)methyl}ammonium chloride, tributyl{(chlorodimethylsilyl)methyl}ammonium bis(fluorosulfonyl)imide, tributyl{(chlorodimethylsilyl)methyl}ammonium bis(trifluoromethanesulfonyl)imide, trihexyl{(chlorodimethylsilyl)methyl}ammonium chloride, trihexyl{(chlorodimethylsilyl)methyl}ammonium bis(fluorosulfonyl)imide, trihexyl{(chlorodimethylsilyl)methyl}ammonium bis(trifluoromethanesulfonyl)imide, trioctyl{(chlorodimethylsilyl)methyl}ammonium chloride, trioctyl{(chlorodimethylsilyl)methyl}ammonium bis(fluorosulfonyl)imide, trioctyl{(chlorodimethylsilyl)methyl}ammonium bis(trifluoromethanesulfonyl)imide, tridecyl {(chlorodimethylsilyl)methyl}ammonium chloride, tridecyl {(chlorodimethylsilyl)methyl}ammonium bis(fluorosulfonyl)imide, tridecyl {(chlorodimethylsilyl)methyl}ammonium bis(trifluoromethanesulfonyl)imide, tridodecyl {(chlorodimethylsilyl)methyl}ammonium chloride, tridodecyl {(chlorodimethylsilyl)methyl}ammonium bis(fluorosulfonyl)imide, tridodecyl {(chlorodimethylsilyl)methyl}ammonium bis(trifluoromethanesulfonyl)imide, 1-{(chlorodimethylsilyl)methyl}-1-methylpyrrolidinium chloride, 1-{(chlorodimethylsilyl)methyl}-1-methylpyrrolidinium bis(fluorosulfonyl)imide, 1-(chlorodimethylsilyl)methyl -1-methylpyrrolidinium bis(trifluoromethanesulfonyl)imide, 1-{(chlorodimethylsilyl)methyl}-1-methylpiperidinium chloride, 1-{(chlorodimethylsilyl)methyl}-1-methylpiperidinium bis(fluorosulfonyl)imide, 1-{(chlorodimethylsilyl)methyl}-1-methylpiperidinium bis(trifluoromethanesulfonyl)imide, 1-{(chlorodimethylsilyl)methyl}pyridinium chloride, 1-{(chlorodimethylsilyl)methyl}pyridinium bis(fluorosulfonyl)imide, 1-{(chlorodimethylsilyl)methyl}pyridinium bis(trifluoromethanesulfonyl)imide, 1-{(chlorodimethylsilyl)methyl}-2-methylpyridinium chloride, 1-{(chlorodimethylsilyl)methyl}-2-methylpyridinium bis(fluorosulfonyl)imide, 1-{(chlorodimethylsilyl)methyl}-2-methylpyridinium bis(trifluoromethanesulfonyl)imide, 1-{(chlorodimethylsilyl)methyl}-3-methylpyridinium chloride, 1-{(chlorodimethylsilyl)methyl}-3-methylpyridinium bis(fluorosulfonyl)imide, 1-{(chlorodimethylsilyl)methyl}-3-methylpyridinium bis(trifluoromethanesulfonyl)imide, 1-{(chlorodimethylsilyl)methyl}-4-methylpyridinium chloride, 1-{(chlorodimethylsilyl)methyl}-4-methylpyridinium bis(fluorosulfonyl)imide, 1-{(chlorodimethylsilyl)methyl}-4-methylpyridinium bis(trifluoromethanesulfonyl)imide, tributyl{(chlorodimethylsilyl)methyl}phosphonium chloride, tributyl{(chlorodimethylsilyl)methyl}phosphonium bis(fluorosulfonyl)imide, tributyl{(chlorodimethylsilyl)methyl}phosphonium bis(trifluoromethanesulfonyl)imide, trihexyl {(chlorodimethylsilyl)methyl}phosphonium chloride, trihexyl {(chlorodimethylsilyl)methane}phosphonium bis(fluorosulfonyl)imide, trihexyl {(chlorodimethylsilyl)methyl}phosphonium bis(trifluoromethanesulfonyl)imide, trioctyl{(chlorodimethylsilyl)methyl}phosphonium chloride, trioctyl{(chlorodimethylsilyl)methyl}phosphonium bis(fluorosulfonyl)imide, trioctyl{(chlorodimethylsilyl)methyl}phosphonium bis(trifluoromethanesulfonyl)imide, 3-{(chlorodimethylsilyl)methyl}-1-methylimidazolium chloride, 3-{(chlorodimethylsilyl)methyl}-1-methylimidazolium bis(fluorosulfonyl)imide, 3-{(chlorodimethylsilyl)methyl}-1-methylimidazolium bis(trifluoromethanesulfonyl)imide, 3-{(chlorodimethylsilyl)methyl}-1-ethylimidazolium chloride, 3-{(chlorodimethylsilyl)methyl}-1-ethylimidazolium bis(fluorosulfonyl)imide, 3-{(chlorodimethylsilyl)methyl}-1-ethylimidazolium bis(trifluoromethanesulfonyl)imide, 3-{(chlorodimethylsilyl)methyl}-1-octylimidazolium chloride, 3-{(chlorodimethylsilyl)methyl}-1-octylimidazolium bis(fluorosulfonyl)imide, 3-{(chlorodimethylsilyl)methyl}-1-octylimidazolium bis(trifluoromethanesulfonyl)imide, 3-{(chlorodimethylsilyl)methyl}-1,2-dimethylimidazolium chloride, 3-{(chlorodimethylsilyl)methyl}-1,2-dimethylimidazolium bis(fluorosulfonyl)imide, 3-{(chlorodimethylsilyl)methyl}-1,2-dimethylimidazolium bis(trifluoromethanesulfonyl)imide, tributyl{3-(chlorodimethylsilyl)propyl}phosphonium chloride, tributyl{3-(chlorodimethylsilyl)propyl}phosphonium bis(fluorosulfonyl)imide, tributyl{3-(chlorodimethylsilyl)propyl}phosphonium bis(trifluoromethanesulfonyl)imide, trioctyl{3-(chlorodimethylsilyl)propyl}phosphonium chloride, trioctyl{3-(chlorodimethylsilyl)propyl}phosphonium bis(fluorosulfonyl)imide, trioctyl{3-(chlorodimethylsilyl)propyl}phosphonium bis(trifluoromethanesulfonyl)imide, tributyl{8-(chlorodimethylsilyl)octyl}phosphonium chloride, tributyl{8-(chlorodimethylsilyl)octyl}phosphonium bis(fluorosulfonyl)imide, tributyl{8-(chlorodimethylsilyl)octyl}phosphonium bis(trifluoromethanesulfonyl)imide, trioctyl{8-(chlorodimethylsilyl)octyl}phosphonium chloride, trioctyl{8-(chlorodimethylsilyl)octyl}phosphonium bis(fluorosulfonyl)imi de, trioctyl{8-(chlorodimethylsilyl)octyl}phosphonium bis(trifluoromethanesulfonyl)imide, tributyl{(methoxydimethylsilyl)methyl}phosphonium chloride, tributyl{(methoxydimethylsilyl)methyl}phosphonium bis(fluorosulfonyl)imide, tributyl{(methoxydimethylsilyl)methyl}phosphonium bis(trifluoromethanesulfonyl)imide, trioctyl{(methoxydimethylsilyl)methyl}phosphonium chloride, trioctyl{(methoxydimethylsilyl)methyl}phosphonium bis(fluorosulfonyl)imide, trioctyl{(methoxydimethylsilyl)methyl}phosphonium bis(trifluoromethanesulfonyl)imide, tributyl{(ethoxydimethylsilyl)methyl}phosphonium chloride, tributyl{(ethoxydimethylsilyl)methyl}phosphonium bis(fluorosulfonyl)imide, tributyl{(ethoxydimethylsilyl)methyl}phosphonium bis(trifluoromethanesulfonyl)imide, trioctyl{(ethoxydimethylsilyl)methyl}phosphonium chloride, trioctyl{(ethoxydimethylsilyl)methyl}phosphonium bis(fluorosulfonyl)imide, trioctyl{(ethoxydimethylsilyl)methyl}phosphonium bis(trifluoromethanesulfonyl)imide, tributyl{(dimethylsilanol)pmethyl}phosphonium chloride, tributyl{(dimethylsilanol)pmethyl}phosphonium bis(fluorosulfonyl)imide, tributyl{(dimethylsilanol)methyl}phosphonium bis(trifluoromethanesulfonyl)imide, trioctyl{(dimethylsilanol)pmethyl}phosphonium chloride, trioctyl{(dimethylsilanol)pmethyl}phosphonium bis(fluorosulfonyl)imide and trioctyl{(dimethylsilanol)pmethyl}phosphonium bis(trifluoromethanesulfonyl)imide.

Of these, from the standpoint of the reactivity with the silanolic hydroxyl group-containing organopolysiloxane compound (6) and the antistatic properties of the resulting organopolysiloxane compound as well as the durability of the antistatic properties, tributyl{(chlorodimethylsilyl)methyl}ammonium chloride, tributyl{(chlorodimethylsilyl)methyl}ammonium bis(trifluoromethanesulfonyl)imide, trioctyl{(chlorodimethylsilyl)methyl}ammonium chloride, trioctyl{(chlorodimethylsilyl)methyl}ammonium bis(trifluoromethanesulfonyl)imide, tributyl{(chlorodimethylsilyl)methyl}phosphonium chloride, tributyl{(chlorodimethylsilyl)methyl}phosphonium bis(trifluoromethanesulfonyl)imide, trioctyl{(chlorodimethylsilyl)methyl}phosphonium chloride, trioctyl{(chlorodimethylsilyl)methyl}phosphonium bis(trifluoromethanesulfonyl)imide, tributyl{3-(chlorodimethylsilyl)propyl}phosphonium chloride, tributyl{3-(chlorodimethylsilyl)propyl}phosphonium bis(trifluoromethanesulfonyl)imide, trioctyl{3-(chlorodimethylsilyl)propyl}phosphonium chloride, trioctyl {3-(chlorodimethylsilyl)propyl}phosphonium bis(trifluoromethanesulfonyl)imide, tributyl{8-(chlorodimethylsilyl)octyl}phosphonium chloride, tributyl{8-(chlorodimethylsilyl)octyl}phosphonium bis(trifluoromethanesulfonyl)imide, trioctyl{8-(chlorodimethylsilyl)octyl}phosphonium chloride and trioctyl{8-(chlorodimethylsilyl)octyl}phosphonium bis(trifluoromethanesulfonyl)imide are preferred; tributyl{(chlorodimethylsilyl)methyl}ammonium bis(trifluoromethanesulfonyl)imide, trioctyl{(chlorodimethylsilyl)methyl}ammonium bis(trifluoromethanesulfonyl)imide, tributyl{(chlorodimethylsilyl)methyl}phosphonium bis(trifluoromethanesulfonyl)imide and trioctyl{(chlorodimethylsilyl)methyl}phosphonium bis(trifluoromethanesulfonyl)imide are more preferred; and tributyl{(chlorodimethylsilyl)methyl}phosphonium bis(trifluoromethanesulfonyl)imide and trioctyl{(chlorodimethylsilyl)methyl}phosphonium bis (trifluoromethanesulfonyl)imide are even more preferred.

Also, in this invention, regarding the silanolic hydroxyl group-containing organopolysiloxane compound (6), from the standpoint of the antistatic properties of the resulting organopolysiloxane compound and the durability of the antistatic properties, Z is more preferably an organopolysiloxane structure of D units alone.

Accordingly, the silanolic hydroxyl group-containing organopolysiloxane compound (6) is preferably one in which the average structural formula is represented by formula (8) below (referred to below as "silanolic hydroxyl group-containing organopolysiloxane compound (8)"). By using such a compound, the resulting organopolysiloxane compound exhibits antistatic properties and a durability thereof that are even better.

[Chem. 18]

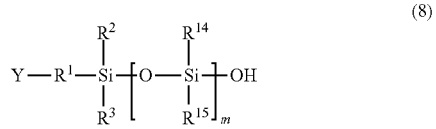

(8)

(wherein $R^1$, $R^2$, $R^3$, $R^{14}$ $R^{15}$, Y and m are as defined above)

A siloxane bond-forming reaction between the silanolic hydroxyl group of the silanolic hydroxyl group-containing organopolysiloxane compound (6) or (8) and the leaving group of the ionic compound (7) may be carried out by a common method known to the art.

More specifically, a reaction that forms a siloxane bond via the reaction mechanism of a dealcoholization, dehydrohalogenation or dehydration reaction is carried out between the silanolic hydroxyl group-containing organopolysiloxane compound (6) or (8) and the ionic compound (7) in the presence of a basic compound.

Various types of basic compounds that are commonly used in siloxane bond-forming reactions may be used as the basic compound.

Specific examples include alkali metal hydrides such as sodium hydride, lithium hydride, potassium hydride and cesium hydride; alkaline earth metal hydrides such as calcium hydride; alkali metal hydroxides such as lithium hydroxide, sodium hydroxide, potassium hydroxide and cesium hydride, as well as aqueous solutions thereof; alkaline earth metal hydroxides such as barium hydroxide and calcium hydroxide, as well as aqueous solutions thereof; alkali metal and alkaline earth metal alkoxides such as potassium t-butoxide and sodium t-butoxide; alkali metal and alkaline earth metal carbonates such as potassium carbonate, sodium carbonate and calcium carbonate; alkali metal and alkaline earth metal bicarbonates such as sodium bicarbonate and potassium bicarbonate; and tertiary amines such as triethylamine, tributylamine, N,N-diisopropylethylamine, tetramethylethylenediamine, pyridine and N,N-dimethyl-4-aminopyridine.

Of these, from the standpoint of the reaction efficiency, tertiary amines such as triethylamine, tributylamine, N,N-diisopropylethylamine, tetramethylethylenediamine, pyridine and N,N-dimethyl-4-aminopyridine are preferred, and triethylamine and tributylamine are more preferred.

The amount of basic compound used is not particularly limited. However, to have the siloxane bond-forming reaction fully proceed and prevent starting material from remaining behind, and also to prevent excess basic compound from remaining behind and thereby increase the storage stability and various properties of the resulting organopolysiloxane compound, the amount of basic compound used per mole of the silanolic hydroxyl groups in the compound of formula (6) is preferably from 0.5 to 10 moles, more preferably from 0.8 to 5 moles, and even more preferably from 0.9 to 2 moles.

A solvent which dissolves and does not react with the starting materials used may be employed in the siloxane bond-forming reaction.

Specific examples include hydrocarbon solvents such as pentane, hexane, heptane, octane, decane and cyclohexane; aromatic solvents such as benzene, toluene and xylene; amide solvents such as formamide, N,N-dimethylformamide, pyrrolidone and N-methylpyrrolidone; ether solvents such as diethyl ether, dibutyl ether, cyclopentyl methyl ether, tetrahydrofuran and 1,4-dioxane; and nitrile solvents such as acetonitrile. These may be used singly, or two or more may be used in combination. Of these, from the standpoint of the reaction efficiency, toluene, xylene, dimethylformamide, cyclopentyl methyl ether, tetrahydrofuran and acetonitrile are preferred. Acetonitrile is more preferred.

The reaction temperature at the time of siloxane bond formation is not particularly limited. However, to obtain a suitable rate of reaction, the temperature is preferably between 0° C. and 100° C., more preferably between 25° C. and 80° C., and even more preferably between 40° C. and 70° C.

The reaction time is not particularly limited, but is typically from 10 minutes to 24 hours.

With regard to the reaction ratio between the silanolic hydroxyl group on the silanolic hydroxyl group-containing organopolysiloxane compound (6) or (8) and the leaving group on the ionic compound (7), to suppress the formation of by-product during the siloxane bond-forming reaction and increase the storage stability and properties of the resulting organopolysiloxane compound, the ratio is preferably from 0.8 to 1.2 moles, and more preferably from 0.9 to 1.1 moles, of the leaving groups per mole of the silanolic hydroxyl groups.

The antistatic agent of the invention includes at least one type of the above-described organopolysiloxane compound (1) of the invention.

The organopolysiloxane compound (1) may be used alone as an antistatic agent, although it may also be used in a form obtained by mixing in other ingredients, such as stabilizers and other additives, solvents and the like.

When other ingredients are included, the content of the organopolysiloxane compound (1) in the antistatic agent is not particularly limited. The content may be suitably set to, for example, 90 wt % or more, 70 wt % or more, 50 wt % or more, 30 wt % or more, 10 wt % or more, 5 wt % or more, or 1 wt % or more.

The solvent is not particularly limited, so long as it does not react with the organopolysiloxane compound (1) and has the ability to dissolve the organopolysiloxane compound (1). From the standpoint of non-reactivity with the organopolysiloxane compound (1), solvency and volatility, illustrative examples include aromatic solvents such as benzene, toluene and xylene; ketone solvents such as acetone, methyl ethyl ketone and methyl isobutyl ketone; ester solvents such as methyl acetate, ethyl acetate, butyl acetate and isobutyl acetate; ether solvents such as diethyl ether, dibutyl ether, cyclopentyl methyl ether, tetrahydrofuran and 1,4-dioxane; and acetonitrile. Of these, toluene, methyl ethyl ketone, methyl isobutyl ketone, ethyl acetate, butyl acetate, dibutyl ether, cyclopentyl methyl ether, tetrahydrofuran and acetonitrile are preferred. Methyl ethyl ketone, methyl isobutyl ketone and acetonitrile are more preferred.

The curable composition of the invention includes an organopolysiloxane compound (1). Compared with conventional antistatic agents, the organopolysiloxane compound (1) of the invention, owing to the structure of this compound, enhances the antistatic properties as well as the durability thereof, in cured products obtained using curable compositions containing the organopolysiloxane compound.

The content of the organopolysiloxane compound (1) in the curable composition of the invention, although not particularly limited, is preferably from about 0.1 wt % to about 10 wt %, and more preferably from 0.5 to 5 wt %, of the curable composition. In cases where the organopolysiloxane compound includes a solvent, the content of the organopolysiloxane compound refers to nonvolatile matter exclusive of the solvent.

The curable composition of the invention preferably includes, as a polymerizable monomer, an ethylenically unsaturated double bond-containing compound.

Examples of the ethylenically unsaturated double bond-containing compound include N-vinylpyrrolidone; mono(meth)acrylates such as 2-hydroxyethyl(meth)acrylate, 2-hydroxypropyl(meth)acrylate, 2-hydroxybutyl(meth)acrylate, n-butyl(meth)acrylate, isobutyl(meth)acrylate, t-butyl (meth)acrylate, glycidyl(meth)acrylate, acryloylmorpholine, tetrahydrofurfuryl acrylate, cyclohexyl(meth)acrylate, 2-ethylhexyl(meth)acrylate, isobornyl(meth)acrylate, isodecyl(meth)acrylate, lauryl(meth)acrylate, tridecyl(meth)acrylate, cetyl (meth)acrylate, stearyl(meth)acrylate, benzyl (meth)acrylate, 2-ethoxyethyl(meth)acrylate, 3-methoxybutyl(meth)acrylate, ethylcarbitol(meth)acrylate, phosphate(meth)acrylate, ethylene oxide-modified phosphate(meth)acrylate, phenoxy(meth)acrylate, ethylene oxide-modified phenoxy(meth)acrylate, propylene oxide-modified phenoxy(meth)acrylate, nonylphenol(meth)acrylate, ethylene oxide-modified nonylphenol(meth)acrylate, propylene oxide-modified nonylphenol(meth)acrylate, methoxy diethylene glycol(meth)acrylate, methoxy polyethylene glycol(meth)acrylate, methoxy propylene glycol (meth)acrylate, 2-(meth)acryloyloxyethyl-2-hydroxypropyl phthalate, 2-hydroxy-3-phenoxypropyl(meth)acrylate, 2-(meth)acryloyloxyethyl hydrogen phthalate, 2-(meth)acryloyloxypropyl hydrogen phthalate, 2-(meth)acryloyloxypropyl hexahydrohydrogen phthalate, 2-(meth)acryloyloxypropyl tetrahydrohydrogen phthalate, dimethylaminoethyl(meth)acrylate, trifluoroethyl(meth)acrylate, tetrafluoropropyl(meth)acrylate, hexafluoropropyl (meth)acrylate, octafluoropropyl(meth)acrylate, octafluoropropyl(meth)acrylate and adamantyl mono(meth)acrylate; di(meth)acrylates such as butanediol di(meth)acrylate, hexanediol di(meth)acrylate, ethoxylated hexanediol di(meth)acrylate, propoxylated hexanediol di(meth)acrylate, diethylene glycol di(meth)acrylate, polyethylene glycol di(meth)acrylate, polypropylene glycol di(meth)acrylate, neopentyl glycol di(meth)acrylate, ethoxylated neopentyl glycol di(meth)acrylate, hydroxypivalic acid neopentyl glycol di(meth)acrylate and 1,3-bis[meth)acryloxymethyl]-1,1,3,3-tetramethyldisiloxane; tri(meth)acrylates such as trimethylolpropane tri(meth)acrylate, ethoxylated trimethylolpropane tri(meth)acrylate, propoxylated trimethylolpropane tri(meth)acrylate, tris(2-hydroxyethyl)isocyanurate tri(meth)acrylate, glycerol tri(meth)acrylate, pentaerythritol tri(meth)acrylate, dipentaerythritol tri(meth)acrylate and ditrimethylolpropane tri(meth)acrylate; and tetrafunctional or higher (meth)acrylates such as pentaerythritol tetra(meth)acrylate, ditrimethylolpropane tetra(meth)acrylate, dipentaerythritol tetra(meth)acrylate, dipentaerythritol penta(meth)acrylate and dipentaerythritol hexa(meth)acrylate.

A curing catalyst such as a photopolymerization initiator may be included in the curable composition of the invention. In addition, various additives such as adhesive modifiers, inorganic and organic ultraviolet absorbers, light stabilizers, storage stability improvers, plasticizers, fillers, pigments and solvents may be added in accordance with the intended purpose of use.

By applying the above-described curable composition of the invention onto the surface of a solid substrate and curing the composition so as to form a coat, a coated solid substrate that is a cured article can be obtained The method of application is not particularly limited. Specific examples of methods that may be used include any that is suitably selected from among known methods such as spray coating, spin coating, dip coating, roller coating, brush coating, bar coating and flow coating.

The solid substrate is not particularly limited. Specific examples include organic polymer substrates such as epoxy resins, phenolic resins, polycarbonates and polycarbonate blends, acrylic resins such as poly(methyl methacrylate), poly(ethylene terephthalate), poly(butylene terephthalate), polyester resins such as unsaturated polyester resins, polyamide resins, polyimide resins, acrylonitrile-styrene copolymers, styrene-acrylonitrile-butadiene copolymers, polyvinyl chloride resins, polystyrene resins, blends of polystyrene and polyphenylene ether, cellulose acetate butyrate and polyethylene resins; metal substrates such as steel plate, paint-coated surfaces, glass, ceramic, concrete, slate board, textiles, lumber, stone, roofing tile, inorganic fillers such as (hollow) silica, titania, zirconia and alumina, and glass fibers and glass fiber products such as glass cloth, glass tape, glass mat and glass paper. There are no particular limitations on the material and shape of the substrate.

EXAMPLES

Examples and Comparative Examples are given below to more concretely illustrate the invention, although the invention is not limited by these Examples.

In the Examples described below, the viscosities of the products are measured values obtained at 25° C. with an Ostwald viscometer, and the contents (wt %) of silanolic hydroxyl groups included in the products were quantitatively determined from the amount of methane gas evolution when a Grignard reagent (methyl magnesium iodide) was made to act on the product. The silicone average composition for each product was computed from the integrated values of the measured $^1$H-NMR and $^{29}$Si-NMR spectra.

In the silicone average compositions shown below, TFSI⁻ represents a bis(trifluoromethanesulfonyl)imide anion.

[1] Synthesis of Organopolysiloxane Compounds

Example 1-1

Synthesis of Organopolysiloxane Compound 1

A 200 mL separable flask equipped with a stirrer, a reflux condenser, a dropping funnel and a thermometer was charged with 4.8 g of a silanolic hydroxyl group-containing organopolysiloxane compound of formula (9) below, 45 g of toluene, 0.03 g of 3,5-di-t-butyl-4-hydroxytoluene and 3.2 g of triethylamine, and heated to 40° C. To this was added dropwise 35.2 g of a 50 wt % toluene solution of tributyl{(chlorodimethylsilyl)methyl}phosphonium bis(trifluoromethanesulfonyl)imide as the ionic compound, and the flask contents were stirred for 2 hours under heating at 50° C. By measuring the silanolic hydroxyl group content, complete consumption down to 0 wt % of the silanolic hydroxyl groups from the silanolic hydroxyl group-containing organopolysiloxane compound serving as the starting material was confirmed, bringing the reaction to completion. Using 30 g of a 10 wt % aqueous Glauber's salt solution, the mixture following reaction completion was subjected to two washing and liquid separation operations, after which distillation under reduced pressure (80° C., 5 mmHg) was carried out for one hour, followed by filtration, giving 17 g of the corresponding Organopolysiloxane Compound 1.

The resulting Organopolysiloxane Compound 1 was a clear colorless liquid that had a viscosity of 90 mm²/s and a silicone average composition represented by formula (10) below.

[Chem. 19]

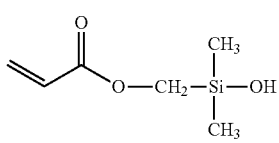
(9)

[Chem. 20]

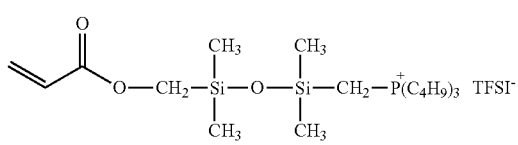
(10)

Example 1-2

Synthesis of Organopolysiloxane Compound 2

A 200 mL separable flask equipped with a stirrer, a reflux condenser, a dropping funnel and a thermometer was charged with 21 g of a silanolic hydroxyl group-containing organopolysiloxane compound of formula (11) below, 10 g of toluene, 40 g of acetonitrile, 0.03 g of 3,5-di-t-butyl-4-hydroxytoluene and 5.8 g of triethylamine, and heated to 40° C. To this was added dropwise 64.8 g of a 50 wt % toluene solution of tributyl{(chlorodimethylsilyl)methyl}phosphonium bis(trifluoromethanesulfonyl)imide as the ionic compound, and the flask contents were stirred for 2 hours under heating at 50° C. By measuring the silanolic hydroxyl group content, complete consumption down to 0 wt % of the silanolic hydroxyl groups from the silanolic hydroxyl group-containing organopolysiloxane compound serving as the starting material was confirmed, bringing the reaction to completion. Using 100 g of a 10 wt % aqueous Glauber's salt solution, the mixture following reaction completion was subjected to two washing and liquid separation operations, after which distillation under reduced pressure (80° C., 5 mmHg) was carried out for one hour, followed by filtration, giving 49 g of the corresponding Organopolysiloxane Compound 2.

The resulting Organopolysiloxane Compound 2 was a clear colorless liquid that had a viscosity of 88 mm²/s and a silicone average composition represented by formula (12) below.

[Chem. 21]

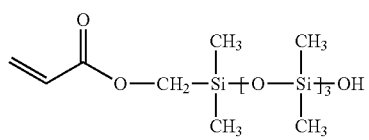
(11)

[Chem. 22]

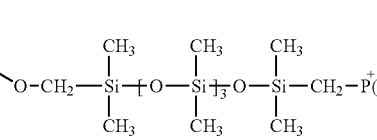
(12)

Example 1-3

Synthesis of Organopolysiloxane Compound 3

A 200 mL separable flask equipped with a stirrer, a reflux condenser, a dropping funnel and a thermometer was charged with 33.2 g of a silanolic hydroxyl group-containing organopolysiloxane compound of formula (13) below, 10 g of toluene, 40 g of acetonitrile, 0.04 g of 3,5-di-t-butyl-4-hydroxytoluene and 5.8 g of triethylamine, and heated to 40° C. To this was added dropwise 64.8 g of a 50 wt % toluene solution of tributyl{(chlorodimethylsilyl)methyl}phosphonium bis(trifluoromethanesulfonyl)imide as the ionic compound, and the flask contents were stirred for 2 hours under heating at 50° C. By measuring the silanolic hydroxyl group content, complete consumption down to 0 wt % of the silanolic hydroxyl groups from the silanolic hydroxyl group-containing organopolysiloxane compound serving as the starting material was confirmed, bringing the reaction to completion. Using 100 g of a 10 wt % aqueous Glauber's salt solution, the mixture following reaction completion was subjected to two washing and liquid separation operations, after which distillation under reduced pressure (80° C., 5 mmHg) was carried out for one hour, followed by filtration, giving 60 g of the corresponding Organopolysiloxane Compound 3.

The resulting Organopolysiloxane Compound 3 was a clear colorless liquid that had a viscosity of 71 mm²/s and a silicone average composition represented by formula (14) below.

[Chem. 23]

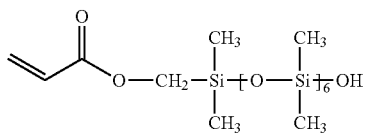

(13)

[Chem. 24]

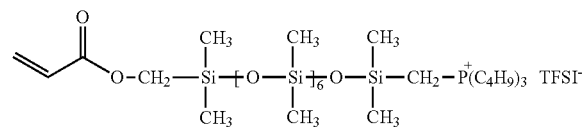

(14)

Example 1-4

Synthesis of Organopolysiloxane Compound 4

A 200 mL separable flask equipped with a stirrer, a reflux condenser, a dropping funnel and a thermometer was charged with 45.4 g of a silanolic hydroxyl group-containing organopolysiloxane compound of formula (15) below, 6.5 g of toluene, 50 g of acetonitrile, 0.05 g of 3,5-di-t-butyl-4-hydroxytoluene and 3.8 g of triethylamine, and heated to 40° C. To this was added dropwise 42.1 g of a 50 wt % toluene solution of tributyl{(chlorodimethylsilyl)methyl}phosphonium bis(trifluoromethanesulfonyl)imide as the ionic compound, and the flask contents were stirred for 2 hours under heating at 50° C. By measuring the silanolic hydroxyl group content, complete consumption down to 0 wt % of the silanolic hydroxyl groups from the silanolic hydroxyl group-containing organopolysiloxane compound serving as the starting material was confirmed, bringing the reaction to completion. Using 100 g of a 10 wt % aqueous Glauber's salt solution, the mixture following reaction completion was subjected to two washing and liquid separation operations, after which distillation under reduced pressure (80° C., 5 mmHg) was carried out for one hour, followed by filtration, giving 58 g of the corresponding Organopolysiloxane Compound 4.

The resulting Organopolysiloxane Compound 4 was a clear colorless liquid that had a viscosity of 81 mm²/s and a silicone average composition represented by formula (16) below.

[Chem. 25]

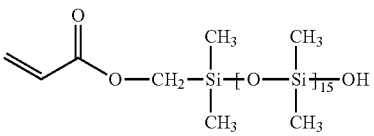

(15)

[Chem. 26]

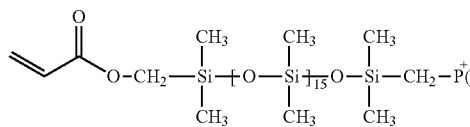

(16)

Example 1-5

Synthesis of Organopolysiloxane Compound 5

Aside from changing the 50 wt % toluene solution of tributyl{(chlorodimethylsilyl)methyl}phosphonium bis(trifluoromethanesulfonyl)imide as the ionic compound to 26.4 g of a 72 wt % acetonitrile solution of tributyl{(chlorodimethylsilyl)methyl}phosphonium chloride, synthesis was carried out in the same way as in Example 1-3, giving 45 g of the corresponding Organopolysiloxane Compound 5.

The resulting Organopolysiloxane Compound 5 was a clear colorless liquid that had a viscosity of 52 mm²/s and a silicone average composition represented by formula (17) below.

[Chem. 27]

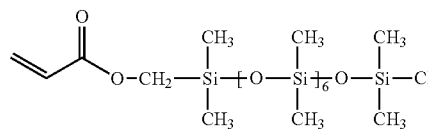

(17)

Example 1-6

Synthesis of Organopolysiloxane Compound 6

Aside from changing the 50 wt % toluene solution of tributyl{(chlorodimethylsilyl)methyl}phosphonium bis(trifluoromethanesulfonyl)imide as the ionic compound to 83.3 g of a 50 wt % toluene solution of trioctyl{(chlorodimethylsilyl)methyl}phosphonium bis(trifluoromethanesulfonyl)imide, synthesis was carried out in the same way as in Example 1-3, giving 70 g of the corresponding Organopolysiloxane Compound 6.

The resulting Organopolysiloxane Compound 5 was a clear colorless liquid that had a viscosity of 68 mm²/s and a silicone average composition represented by formula (17) below.

[Chem. 28]

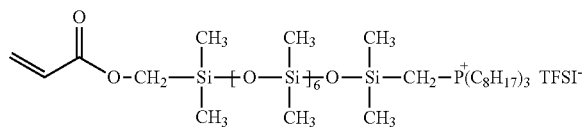

(18)

Example 1-7

Synthesis of Organopolysiloxane Compound 7

Aside from changing the 50 wt % toluene solution of tributyl{(chlorodimethylsilyl)methyl}phosphonium bis(trifluoromethanesulfonyl)imide as the ionic compound to 35.3 g of a 80 wt % acetonitrile solution of trioctyl{(chlorodimethylsilyl)methyl}phosphonium chloride, synthesis was carried out in the same way as in Example 1-3, giving 55 g of the corresponding Organopolysiloxane Compound 7.

The resulting Organopolysiloxane Compound 7 was a clear colorless liquid that had a viscosity of 170 mm²/s and a silicone average composition represented by formula (19) below.

[Chem. 29]

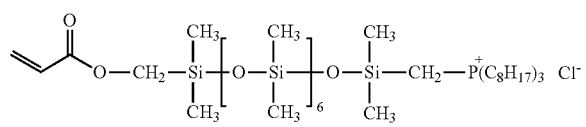

(19)

Example 1-8

Synthesis of Organopolysiloxane Compound 8

Aside from changing the silanolic hydroxyl group-containing organopolysiloxane compound of formula (13) to

[Chem. 32]

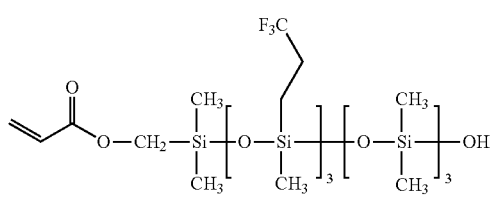

60.3 g of the silanolic hydroxyl group-containing organopolysiloxane compound of formula (20) below, synthesis was carried out in the same way as in Example 1-3, giving 79 g of the corresponding Organopolysiloxane Compound 8.

The resulting Organopolysiloxane Compound 8 was a hazy colorless liquid that had a viscosity of 65 mm²/s and a silicone average composition represented by formula (21) below.

[Chem. 30]

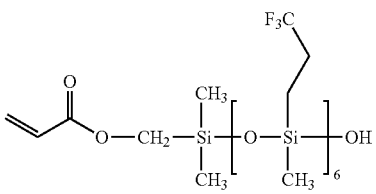

(20)

[Chem. 31]

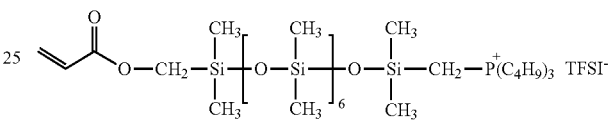

(21)

Example 1-9

Synthesis of Organopolysiloxane Compound 9

Aside from changing the silanolic hydroxyl group-containing organopolysiloxane compound of formula (13) to 46.7 g of the silanolic hydroxyl group-containing organopolysiloxane compound of formula (22) below, synthesis was carried out in the same way as in Example 1-3, giving 69 g of the corresponding Organopolysiloxane Compound 9.

The resulting Organopolysiloxane Compound 9 was a hazy colorless liquid that had a viscosity of 72 mm²/s and a silicone average composition represented by formula (23) below.

(22)

[Chem. 33]

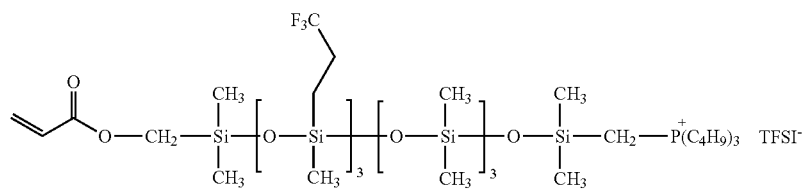

(23)

Example 1-10

Synthesis of Organopolysiloxane Compound 10

A 200 mL separable flask equipped with a stirrer, a reflux condenser, a dropping funnel and a thermometer was charged with 34.0 g of a silanolic hydroxyl group-containing organopolysiloxane compound of formula (24) below, 10 g of toluene, 40 g of acetonitrile, 0.04 g of 3,5-di-t-butyl-4-hydroxytoluene and 5.8 g of triethylamine, and heated to 40° C.

To this was added dropwise 83.3 g of a 50 wt % toluene solution of trioctyl{(chlorodimethylsilyl)methyl}phosphonium bis(trifluoromethanesulfonyl)imide as an ionic compound, and the flask contents were stirred for 2 hours under heating at 50° C. By measuring the silanolic hydroxyl group content, complete consumption down to 0 wt % of the silanolic hydroxyl groups from the silanolic hydroxyl group-containing organopolysiloxane compound serving as the starting material was confirmed, bringing the reaction to completion. Using 100 g of a 10 wt % aqueous Glauber's salt solution, the mixture following reaction completion was subjected to two washing and liquid separation operations, after which distillation under reduced pressure (80° C., 5 mmHg) was carried out for one hour, followed by filtration, giving 72 g of the corresponding Organopolysiloxane Compound 10.

The resulting Organopolysiloxane Compound 10 was a clear colorless liquid that had to a viscosity of 70 mm$^2$/s and a silicone average composition represented by formula (25) below.

[Chem. 34]

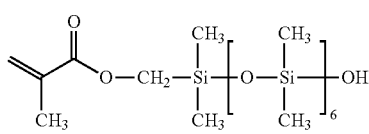

(24)

[Chem. 35]

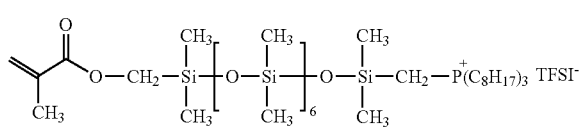

(25)

Example 1-11

Synthesis of Organopolysiloxane Compound 11

Aside from changing the silanolic hydroxyl group-containing organopolysiloxane compound of formula (24) to 33.2 g of the silanolic hydroxyl group-containing organopolysiloxane compound of formula (26) below, synthesis was carried out in the same way as in Example 1-10, giving 68 g of the corresponding Organopolysiloxane Compound 11.

The resulting Organopolysiloxane Compound 11 was a clear colorless liquid that had a viscosity of 88 mm$^2$/s and a silicone average composition represented by formula (27) below.

[Chem. 36]

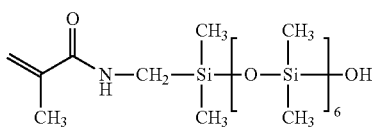

(26)

[Chem. 37]

(27)

Example 1-12

Synthesis of Organopolysiloxane Compound 12

Aside from changing the silanolic hydroxyl group-containing organopolysiloxane compound of formula (24) to 33.9 g of the silanolic hydroxyl group-containing organopolysiloxane compound of formula (28) below, synthesis was carried out in the same way as in Example 1-10, giving 71 g of the corresponding Organopolysiloxane Compound 12.

The resulting Organopolysiloxane Compound 12 was a clear colorless liquid that had a viscosity of 85 mm$^2$/s and a silicone average composition represented by formula (29) below.

[Chem. 38]

(28)

[Chem. 39]

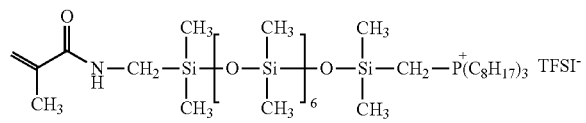

(29)

[Chem. 40]

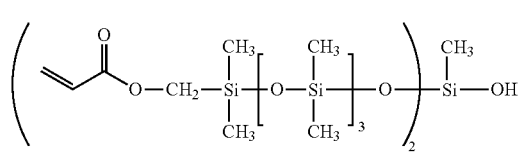

(30)

[Chem. 41]

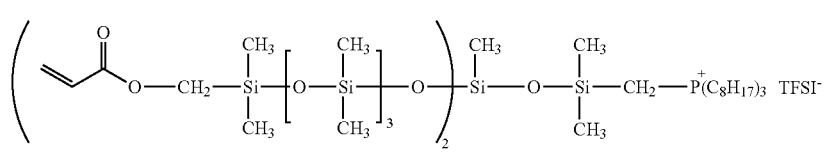

(31)

Example 1-13

Synthesis of Organopolysiloxane Compound 13

Aside from changing the silanolic hydroxyl group-containing organopolysiloxane compound of formula (24) to 69.6 g of the silanolic hydroxyl group-containing organopolysiloxane compound of formula (30) below, synthesis was carried out in the same way as in Example 1-10, giving 95 g of the corresponding Organopolysiloxane Compound 13.

The resulting Organopolysiloxane Compound 13 was a clear colorless liquid that had a viscosity of 435 mm²/s and a silicone average composition represented by formula (31) below.

Example 1-14

Synthesis of Organopolysiloxane Compound 14

Aside from changing the silanolic hydroxyl group-containing organopolysiloxane compound of formula (24) to 65.3 g of the silanolic hydroxyl group-containing organopolysiloxane compound of formula (32) below, synthesis was carried out in the same way as in Example 1-10, giving 90 g of the corresponding Organopolysiloxane Compound 14.

The resulting Organopolysiloxane Compound 14 was a clear colorless liquid that had a viscosity of 710 mm²/s and a silicone average composition represented by formula (33) below.

[Chem. 42]

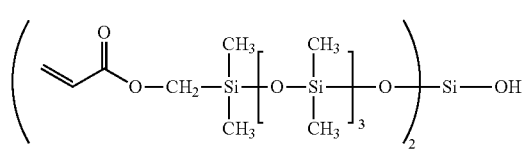

(32)

[Chem. 43]

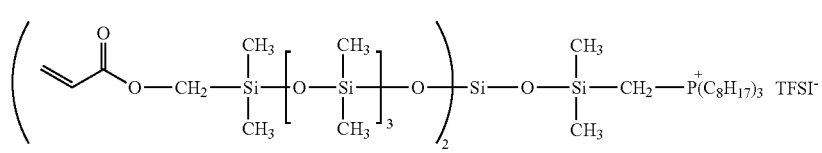

(33)

Comparative Example 1-1

Synthesis of Organopolysiloxane Compound 15

A 500 mL separable flask equipped with a stirrer, a reflux condenser, a dropping funnel and a thermometer was charged with 51.6 g (0.4 mol) of dimethyldimethoxysilane, 40 g of isopropyl alcohol and 30.8 g (0.05 mol) of 1-(3-trimethoxysilylpropyl)-1,1,1-tributylphosphonium bis(trifluoromethanesulfonyl)imide. To this was added dropwise at room temperature 8.5 g of 0.1 N hydrochloric acid, and the flask contents were stirred for 16 hours at 25° C. Following reaction completion, the mixture was concentrated by distillation under reduced pressure (80° C., 5 mmHg) for 3 hours, and the resulting concentration residue was twice washed and liquid-separated with 80 g of n-hexane. This was followed by 1 hour of concentration by distillation under reduced pressure (80° C., 5 mmHg), giving 35 g of the corresponding Organopolysiloxane Compound 15.

The resulting Organopolysiloxane Compound 15 was a clear colorless liquid that had a viscosity of 70 mm$^2$/s.

Comparative Example 1-2

Synthesis of Organopolysiloxane Compound 16

A 500 mL separable flask equipped with a stirrer, a reflux condenser, a dropping funnel and a thermometer was charged with 130.3 g (1.1 mol) of dimethyldimethoxysilane, 42.2 g (0.31 mol) of methyltrimethoxysilane, 135 g of isopropyl alcohol and 100 g (0.15 mol) of 1-(3-trimethoxysilylpropyl)-1,1,1-tributylphosphonium bis(trifluoromethanesulfonyl)imide. To this was added dropwise at room temperature 30.0 g of 0.1 N hydrochloric acid, and the flask contents were stirred for 16 hours at 25° C. Following reaction completion, the mixture was concentrated by distillation under reduced pressure (80° C., 5 mmHg) for 3 hours, and the resulting concentration residue was twice washed and liquid-separated with 270 g of n-hexane. This was followed by 1 hour of concentration by distillation under reduced pressure (80° C., 5 mmHg), giving 120 g of the corresponding Organopolysiloxane Compound 16.

The resulting Organopolysiloxane Compound 16 was a hazy colorless liquid that had a viscosity of 980 mm$^2$/s.

[2] Preparation of Curable Compositions and Cured Articles Thereof

The ingredients used when preparing the curable compositions and the cured articles thereof are described below.

[Ethylenically Unsaturated Double Bond-Containing Compound]
  Dipentaerythritol hexaacrylate
[Curing Catalyst (Photopolymerization Initiator)]
  2-Hydroxy-2-methylpropiophenone
[Solvent]
  Methyl ethyl ketone

[Antistatic Agent]
  Organopolysiloxane compound:
    Organopolysiloxane compounds obtained from above Examples 1-1 to 1-14 and Comparative Examples 1-1 and 1-2

Example 2-1

A curable composition was obtained by mixing together 5.0 g of dipentaerythritol hexaacrylate, 5.0 g of methyl ethyl ketone, 0.25 g of 2-hydroxy-2-methylpropiophenone and 0.10 g of Organopolysiloxane Compound 1 obtained in Example 1-1 above. Next, the resulting curable composition was applied with a bar coater onto one side of a 100 µm thick polyethylene terephthalate film so as to give a coat thickness when dry of about 5 µm. The applied coat was then cured by irradiating the coated side of the film in a nitrogen atmosphere with ultraviolet light from a high vapor-pressure mercury UV lamp (120 W/cm$^2$) to a cumulative exposure dose of about 600 mJ/cm$^2$, thereby producing as the cured article a test piece having a coat obtained by coating with an electron beam-curable resin.

Examples 2-2 to 2-14 and Comparative Examples 2-1 and 2-2

Aside from changing Organopolysiloxane Compound 1 to Organopolysiloxane Compounds 2 to 16 obtained in Examples 1-2 to 1-14 and Comparative Examples 1-1 and 1-2, curable compositions and cured articles thereof were produced in the same way as in Example 2-1.

Comparative Example 2-3

Aside from changing Organopolysiloxane Compound 1 to 0.10 g of methyltrioctylammonium bis(trifluoromethanesulfonyl)imide, a curable composition and a cured article thereof were produced in the same way as in Example 2-1.

Comparative Example 2-4

Aside from not using Organopolysiloxane Compound 1, a curable composition and a cured article thereof were produced in the same way as in Example 2-1.

Evaluations were carried out by the methods shown below on the cured articles fabricated in the above manner.

[Antistatic Properties]
The surface resistivity (Ω/□) at the coating surface of the test piece was measured using the Hiresta UP (MCP-HT450) from Mitsubishi Chemical Analytech Co., Ltd. under the following conditions: 25±3° C.; humidity, 45±5%; applied voltage, 500 V. The results are shown in Tables 1 and 2 below.

[Durability]
The cured articles that were fabricated were immersed for 5 hours in ion-exchanged water at 25±3° C., following which water droplets were wiped off and the surface resistivity (Ω/□) was measured in the same way as above. The results are shown in Tables 1 and 2 below.

TABLE 1

| | Example | | | | | | | | |
|---|---|---|---|---|---|---|---|---|---|
| | 2-1 | 2-2 | 2-3 | 2-4 | 2-5 | 2-6 | 2-7 | 2-8 | 2-9 |
| Organopolysiloxane compound | 1 | 2 | 3 | 4 | 5 | 6 | 7 | 8 | 9 |

TABLE 1-continued

| | Example | | | | | | | | |
|---|---|---|---|---|---|---|---|---|---|
| | 2-1 | 2-2 | 2-3 | 2-4 | 2-5 | 2-6 | 2-7 | 2-8 | 2-9 |
| Antistatic properties | $3 \times 10^{12}$ | $5 \times 10^{11}$ | $1 \times 10^{11}$ | $4 \times 10^{11}$ | $3 \times 10^{11}$ | $1 \times 10^{11}$ | $2 \times 10^{11}$ | $6 \times 10^{11}$ | $4 \times 10^{11}$ |
| Durability | $6 \times 10^{12}$ | $1 \times 10^{12}$ | $8 \times 10^{11}$ | $8 \times 10^{11}$ | $1 \times 10^{12}$ | $5 \times 10^{11}$ | $9 \times 10^{11}$ | $9 \times 10^{11}$ | $9 \times 10^{11}$ |

TABLE 2

| | Example | | | | | Comparative Example | | | |
|---|---|---|---|---|---|---|---|---|---|
| | 2-10 | 2-11 | 2-12 | 2-13 | 2-14 | 2-1 | 2-2 | 2-3 | 2-4 |
| Organo-polysiloxane compound | 10 | 11 | 12 | 13 | 14 | 15 | 16 | methyltrioctylammonium bis(trifluoromethane-sulfonyl)imide | — |
| Antistatic properties | $1 \times 10^{11}$ | $2 \times 10^{11}$ | $4 \times 10^{11}$ | $8 \times 10^{11}$ | $9 \times 10^{11}$ | $3 \times 10^{11}$ | $5 \times 10^{11}$ | $>10^{14}$ | $>10^{14}$ |
| Durability | $7 \times 10^{11}$ | $6 \times 10^{11}$ | $8 \times 10^{11}$ | $1 \times 10^{12}$ | $1 \times 10^{12}$ | $>10^{14}$ | $>10^{14}$ | $>10^{14}$ | $>10^{14}$ |

As shown in Tables 1 and 2, compared with the organopolysiloxane compound and methyltrioctylammonium bis(trifluoromethanesulfonyl)imide obtained in Comparative Examples 1-1 and 1-2, the organopolysiloxane compounds obtained in Examples 1-1 to 1-14 imparted higher antistatic properties to electron beam-curable resins and the durability of the antistatic properties was excellent.

The invention claimed is:

1. An organopolysiloxane compound represented by average structural formula (1)

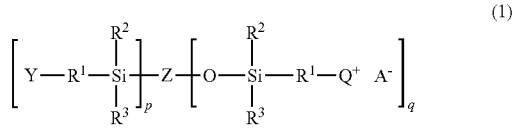

wherein Z is a single bond or a 2 to 20-valent group which includes an organopolysiloxane structure,
each $R^1$ is independently a single bond or a substituted or unsubstituted alkylene group of 1 to 20 carbon atoms,
$R^2$ and $R^3$ are each independently a substituted or unsubstituted alkyl group of 1 to 10 carbon atoms or aryl group of 6 to 10 carbon atoms,
each Y is independently a polymerizable reactive group-containing monovalent hydrocarbon group,
p is a number from 1 to 10, q is a number from 1 to 10, and p+q is a number from 2 to 20 corresponding to the valence of Z, with the proviso that when Z is a single bond, p and q are both 1,
$A^{31}$ is a monovalent anion, and
$Q^+$ is a monovalent cationic group represented by any one of formulas (3) to (4) below $$R^8-\overset{R^7}{\underset{R^9}{\overset{|}{N^+}}}-* \quad (3)$$

-continued $$\underset{R^{12}}{\overset{R^{10}}{\underset{\phantom{R^{12}}}{N}}} \overset{R^{11}}{\underset{R^{13}}{\overset{\phantom{|}}{\overset{+}{N}}}}-* \quad (4)$$

wherein $R^7$ to $R^{10}$ are each independently an alkyl group of 1 to 20 carbon atoms, an aryl group of 6 to 20 carbon atoms or an aralkyl group of 7 to 20 carbon atoms; $R^{11}$ to $R^{13}$ are each independently a hydrogen atom, an alkyl group of 1 to 20 carbon atoms or an aryl group of 6 to 20 carbon atoms; $R^7$ and $R^8$ may mutually bond to form, together with the phosphorus atom, a phosphorane ring which may have a substituent, a phosphorinane ring which may have a substituent or a phosphorine ring which may have a substituent; and * represents a site available for bonding; with the provisos that when $R^7$ and $R^8$ mutually bond to form a phosphorine ring, $R^9$ does not exist.

2. The organopolysiloxane compound of claim 1, wherein the polymerizable reactive group Y is of one type selected from (meth)acryloyloxy groups and (meth)acrylamide groups.

3. The organopolysiloxane compound of claim 1, wherein $A^-$ is a fluorine-containing anion or a halide ion.

4. The organopolysiloxane compound of claim 1, wherein $A^-$ is a trifluoromethanesulfonic acid anion, a nonafluorobutanesulfonic acid anion, a bis(fluorosulfonyl)imide anion, a bis(trifluoromethanesulfonyl)imide anion, a tetrafluoroborate anion, a hexafluorophosphate anion, a chloride ion, a bromide ion or an iodide ion.

5. The organopolysiloxane compound of claim 1 which is represented by average structural formula (5)

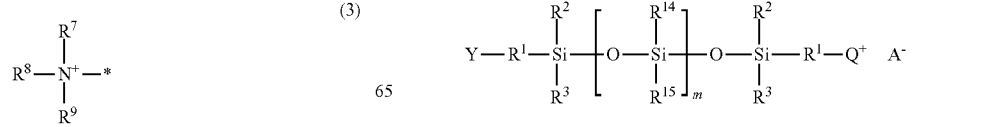

wherein $R^1$, $R^2$, $R^3$, Y, $A^-$ and $Q^+$ are as defined above, $R^{14}$ and $R^{15}$ are each independently a substituted or unsubstituted alkyl group of 1 to 20 carbon atoms or aryl group of 6 to 10 carbon atoms, and m is a number of 0 or more.

6. A method of preparing an organopolysiloxane represented by average structural formula (1)

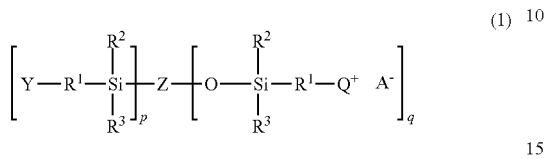
(1)

wherein Z is a single bond or a 2 to 20-valent group which includes an organopolysiloxane structure,
each $R^1$ is independently a single bond or a substituted or unsubstituted alkylene group of 1 to 20 carbon atoms,
$R^2$ and $R^3$ are each independently a substituted or unsubstituted alkyl group of 1 to 10 carbon atoms or aryl group of 6 to 10 carbon atoms,
each Y is independently a polymerizable reactive group-containing monovalent hydrocarbon group, p1 is a number from 1 to 10, q is a number from 1 to 10, and p+q is a number from 2 to 20 corresponding to the valence of Z, with the proviso that when Z is a single bond, p and q are both 1,
$A^-$ is a monovalent anion, and
$Q+$ is a monovalent cationic group represented by any one of formulas (2) (3) to (4) below:

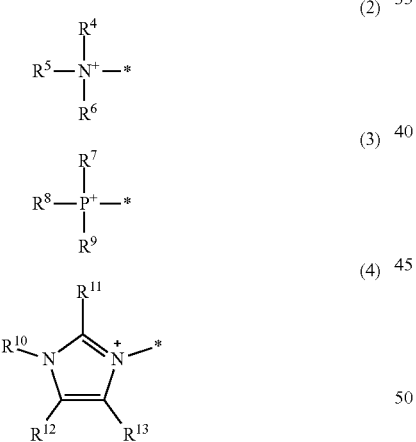
(2)
(3)
(4)

wherein $R^4$ to $R^{10}$ are each independently an alkyl group of 1 to 20 carbon atoms, an aryl group of 6 to 20 carbon atoms or an aralkyl group of 7 to 20 carbon atoms; $R^{11}$ to $R^{13}$ are each independently a hydrogen atom, an alkyl group of 1 to 20 carbon atoms or an aryl group of 6 to 20 carbon atoms; $R^4$ and $R^5$ may mutually bond to form, together with the nitrogen atom, a pyrrolidine ring which may have a substituent, a piperidine ring which may have a substituent or a pyridine ring which may have a substituent; $R^7$ and $R^8$ may mutually bond to form, together with the phosphorus atom, a phosphorane ring which may have a substituent, a phosphorinane ring which may have a substituent or a phosphorine ring which may have a substituent; and represents a site available for bonding; with the provisos that when $R^4$ and $R^5$ mutually bond to form a pyridine ring, $R^6$ does not exist, and when $R^7$ and $R^8$ mutually bond to form a phosphorine ring, $R^9$ does not exist;
wherein the method comprises the step of reacting a polymerizable reactive group and silanolic hydroxyl group-containing organopolysiloxane compound of average structural formula (6)

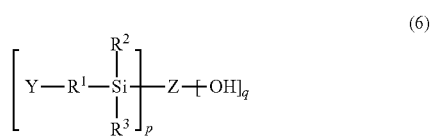
(6)

wherein wherein $R^1$, $R^2$, $R^3$, Y, p, q and Z are as defined above, and OH is a silanolic hydroxyl group with a compound of formula (7)

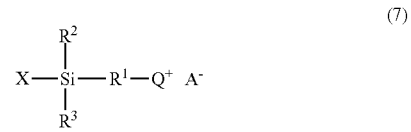
(7)

wherein wherein $R^1$, $R^2$, $R^3$, A and Q+ are as defined above, and X is a leaving group selected from alkoxy groups of 1 to 10 carbon atoms, halogen atoms and a hydroxyl group having a functional group capable of reacting with the silanolic hydroxyl group and having an ionic group.

7. A method of preparing an organopolysiloxane compound represented by average structural formula (5)

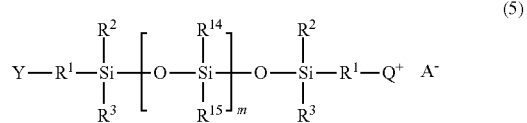
(5)

wherein each $R^1$ is independently a single bond or a substituted or unsubstituted alkylene group of 1 to 20 carbon atoms,
$R^2$ and $R^3$ are each independently a substituted or unsubstituted alkyl group of 1 to 10 carbon atoms or aryl group of 6 to 10 carbon atoms,
Y is a polymerizable reactive group-containing monovalent hydrocarbon group,
$A^-$ is a monovalent anion,
Q+ is a monovalent cationic group represented by any one of formulas (2) (3) to (4) below:

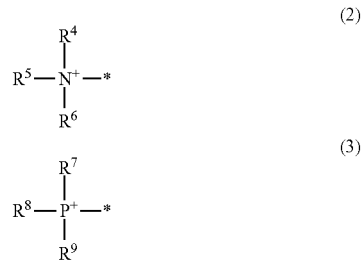
(2)
(3)

-continued

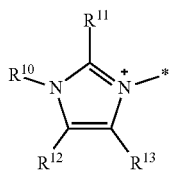 (4)

wherein $R^4$ to $R^{10}$ are each independently an alkyl group of 1 to 20 carbon atoms, an aryl group of 6 to 20 carbon atoms or an aralkyl group of 7 to 20 carbon atoms; $R^{11}$ to $R^{13}$ are each independently a hydrogen atom, an alkyl group of 1 to 20 carbon atoms or an aryl group of 6 to 20 carbon atoms; $R^4$ and $R^5$ may mutually bond to form, together with the nitrogen atom, a pyrrolidine ring which may have a substituent, a piperidine ring which may have a substituent or a pyridine ring which may have a substituent; $R^7$ and $R^8$ may mutually bond to form, together with the phosphorus atom, a phosphorane ring which may have a substituent, a phosphorinane ring which may have a substituent or a phosphorine ring which may have a substituent; and
* represents a site available for bonding; with the provisos that when $R^4$ and $R^5$ mutually bond to form a pyridine ring, $R^6$ does not exist, and when $R^7$ and $R^8$ mutually bond to form a phosphorine ring, $R^9$ does not exist, $R^{14}$ and $R^{15}$ are each independently a substituted or unsubstituted alkyl group of 1 to 20 carbon atoms or aryl group of 6 to 10 carbon atoms, and m is a number of 0 or more;

wherein the method comprises the step of reacting a polymerizable reactive group and silanolic hydroxyl group-containing organopolysiloxane compound of average structural formula (8)

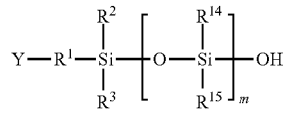 (8)

wherein $R^1$, $R^2$, $R^3$, $R^{14}$, $R^{15}$, Y and m are as defined above with a compound of formula (7)

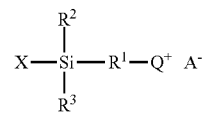 (7)

wherein $R^1$, $R^2$, $R^3$, $A^1$, and Q+ and X are as defined above, and X is a leaving group selected from alkoxy groups of 1 to 10 carbon atoms, halogen atoms and a hydroxyl group having a functional group capable of reacting with the silanolic hydroxyl group and having an ionic group.

8. An antistatic agent comprising the organopolysiloxane compound of claim 1.

9. A curable composition comprising the organopolysiloxane compound of claim 1.

10. A coating material comprising the curable composition of claim 9.

11. A cured article obtained by curing the curable composition of claim 9.

12. A cured article having a coat obtained using the coating material of claim 10.

* * * * *